United States Patent [19]

Paoletti

[11] Patent Number: 5,174,993
[45] Date of Patent: Dec. 29, 1992

[54] RECOMBINANT AVIPOX VIRUS AND IMMUNOLOGICAL USE THEREOF

[75] Inventor: Enzo Paoletti, Albany, N.Y.

[73] Assignee: Health Research Inc., Albany, N.Y.

[21] Appl. No.: 537,890

[22] Filed: Jun. 14, 1990

Related U.S. Application Data

[60] Continuation-in-part of Ser. No. 537,882, Jun. 14, 1990, Pat. No. 5,110,587, and a continuation of Ser. No. 234,390, Aug. 23, 1988, abandoned, which is a continuation-in-part of Ser. No. 186,054, Apr. 25, 1988, abandoned, which is a continuation-in-part of Ser. No. 110,335, Oct. 20, 1987, abandoned, which is a continuation-in-part of Ser. No. 90,711, Aug. 28, 1987, abandoned, said Ser. No. 537,882, is a continuation of Ser. No. 90,209, Aug. 27, 1987, abandoned, which is a division of Ser. No. 662,135, Jun. 19, 1984, Pat. No. 4,722,848, which is a continuation-in-part of Ser. No. 446,824, Dec. 8, 1982, Pat. No. 4,603,112, which is a continuation-in-part of Ser. No. 334,456, Dec. 24, 1981, Pat. No. 4,769,330.

[51] Int. Cl.$^5$ ............... A61K 39/295; A61K 39/275; C12N 7/01; C12N 15/86

[52] U.S. Cl. .................................. 424/89; 435/235.1; 435/320.1; 424/93; 935/32; 935/57; 935/65

[58] Field of Search ............... 435/235.1, 69.1, 69.3, 435/172.3, 320.1, 91; 424/89, 93; 935/32, 57, 65

[56] References Cited

U.S. PATENT DOCUMENTS

| | | | |
|---|---|---|---|
| 4,603,112 | 7/1986 | Paoletti et al. | 435/235.1 |
| 4,663,281 | 5/1987 | Gillies et al. | 435/69.1 |
| 4,722,848 | 2/1988 | Paoletti et al. | 424/89 |
| 4,736,866 | 4/1988 | Leder et al. | 800/2 |
| 4,738,846 | 4/1988 | Rose et al. | 424/87 |
| 4,769,330 | 9/1988 | Paoletti et al. | 435/172.3 |

FOREIGN PATENT DOCUMENTS

| | | |
|---|---|---|
| 0052002 | 5/1982 | European Pat. Off. |
| 0162757 | 11/1985 | European Pat. Off. |
| 0216564 | 4/1987 | European Pat. Off. |
| 0227414 | 7/1987 | European Pat. Off. |
| 0261940 | 3/1988 | European Pat. Off. |
| 0284416 | 9/1988 | European Pat. Off. |
| 0314569 | 5/1989 | European Pat. Off. |
| 0324350 | 7/1989 | European Pat. Off. |
| 0330781 | 9/1989 | European Pat. Off. |
| 0344808 | 12/1989 | European Pat. Off. |
| 0353851 | 2/1990 | European Pat. Off. |
| 88/02022 | 3/1988 | PCT Int'l Appl. |
| 88/02027 | 3/1988 | PCT Int'l Appl. |
| 89/03879 | 5/1989 | PCT Int'l Appl. |
| 89/07644 | 8/1989 | PCT Int'l Appl. |
| 89/08716 | 9/1989 | PCT Int'l Appl. |
| 89/12684 | 12/1989 | PCT Int'l Appl. |
| 90/02190 | 3/1990 | PCT Int'l Appl. |
| 90/10693 | 9/1990 | PCT Int'l Appl. |
| 2222165 | 2/1990 | United Kingdom. |
| 86/65806 | 10/1986 | World Int. Prop. O. |

OTHER PUBLICATIONS

Babinet, C. et al. 1985. *Science* vol. 230 pp. 1160–1163.
Ballay, A. et al 1985. *The EMBO Journal* vol. 4 pp. 3861–3865.
Salter, D. W. et al. 1987. *Virology* vol. 157 pp. 236–240.
Watanabe, S. et al. 1983. *Molecular and Cellular Biology* vol. 3 pp. 2241–2249.
Mann, R. et al. 1983. *Cell* vol. 33 pp. 153–159.
Schachter, J. 1980. In *Manual of Clinical Microbiology* 3rd ed. E. H. Lennette et al, American Society for Microbiology, pp. 357–364. H. R. 1984. *Biological Abstr.* vol. 77 p. 402 Abstr. 3598.
Langridge, W. H. R. 1984. *Biological Abstr.* vol. 77 p. 402 Abstr. 3598.
Nakano et al Proc. Natl. Acad Sci vol. 79 (1982) pp. 1593–1596.
Smith et al, Proc. Natl. Acad Sci vol. 80 (1983) 7155–7159.
Pouwells et al Cloning Vectors (1985) pVIII-A-a-i-9.
Graham, Tibtech 8, 85–87 (Apr., 1990).
Prevec et al., J. gen. Virol. 70, 429–434 (1989).
Tartaglia et al., Immunochemistry of Viruses II, edited by M. H. V. van Regenmortel et al. (Elsevier Science Publishers), 125–151 (1990).
Melnick, Virology, Second Edition, edited by B. N. Fields (Raven Press, N.Y.), Chapter 21, 549–605 1990).
Kitson et al., J. Virol. 65, 3068–3075 (1991).
Hagino-Yamagishi, Chapter 14, New Aspects of Positive-Strand RNA Viruses (American Society for Microbiology, Washington, D.C.), edited by M. A. Brinton et al.
Hagino-Yamagishi et al., J. Virol. 63, 5386–5392 (1989).
Choi et al., J. Virol. 65, 2875–2883 (1991).
Geigenmüller-Gnirke et al., Proc. Natl. Acad. Sci. U.S.A. 88, 3253–3257 (1991).

Levis et al., J. Virol. 64, 1726–1733 (1990).
Pattnaik et al., Proc. Natl. Acad. Sci. U.S.A. 88, 1379–1383 (1991).
Pattnaik et al., J. Virol 64, 2948–2957 (1990).
Huang et al., J. Virol. 64, 5669–5673 (1990).
Wild et al., Vaccine 8, 441 (1991).
Boursnell et al., Virus Research 1, 303–313 (1984).

(List continued on next page.)

*Primary Examiner*—Richard A. Schwartz
*Assistant Examiner*—Mary E. Mosher
*Attorney, Agent, or Firm*—Curtis, Morris & Safford

[57] ABSTRACT

The present invention provides a method for inducing an immunological response in a vertebrate to a pathogen by inoculating the vertebrate with a synthetic recombinant avipox virus modified by the presence, in a non-essential region of the avipox genome, of DNA from any source which codes for and expresses an antigen of the pathogen. The present invention further provides a synthetic recombinant avipox virus modified by the insertion therein of DNA from any source, and particularly from a non-avipox source, into a non-essential region of the avipox genome.

3 Claims, No Drawings

OTHER PUBLICATIONS

Paoletti et al., Proc. Natl. Acad. Sci. USA 81, 193–197 (1984).
Chemical Abstracts 72095k.
Biological Abstracts 3809.
Chemical Abstracts 103510m.
Chemical Abstracts 133233q.
Fenner et al. (1987) In: Veterinary Virology, Academic Press, pp. 403–404.
Bruner, D. W. (1963) The pox diseases of man and animals. In: Diseases Transmitted from Animals to Man, (ed. Hull, T. G.), Charles C. Thomas, Publisher p. 394.
Lyles et al. (1976) Cellular fatty acids during fowlpox virus infection of three different host systems, Virology 70, p. 227.
Classification and Nomenclature of Viruses, Intervirology 17, p. 43.
Beveridge, W. I. B. and L. Hart (1985) Animal Health in Australia, vol. 7, p. 58.
Gillespie, J. H. and J. F. Timoney (1981) Hagan and Bruner's Infectious Dieases of Domestic Animals. Cornell University Press, p. 531.
Buxton, A. (1977) Animal Microbiology. Blackwell Scientific Publications, p. 693.
Andrewes et al. (1978) Viruses of Vertebrates. Cassell & Co. Ltd, p. 374.
Hofstad et al. (1972) Diseases of Poultry. The Iowa University Press, p. 707.
Rhodes, A. J. and C. E. Van Rooyen (1968) Textbook of Virology. The Williams and Wilkins Co.
Merck Veterinary Manual (1986) ed. Fraser et al., p. 1324.
Dalrymple, J. M. (1989) Vaccinia-vectored vaccines for exotic disease immunization programmes. In: Vaccinia-vectored Vaccines–Risks and Benefits, (ed. F. A. Murphy), 2nd Forum in Virology, Institut Pasteur, Elsevier, p. 479.
Esposito, J. J. and F. A. Murphy (1989) Infectious recombinant vectored virus vaccines. In: Vaccine Biotechnology, vol. 33 (ed. Bittle, J. L. and F. A. Murphy), Academic Press, p. 235.
Mackett, M. and G. L. Smith (1986) Vaccinia virus expression vectors, J. gen Virol. 67, p. 2078.

RECOMBINANT AVIPOX VIRUS AND IMMUNOLOGICAL USE THEREOF

This application is a continuation of application Ser. No. 07/234,390 filed Aug. 23, 1988, now abandoned, which is a continuation-in-part of application Ser. No. 186,054 filed Apr. 25, 1988, now abandoned, which in turn is a continuation-in-part of application Ser. No. 110,335 filed Oct. 20, 1987, now abandoned, which in turn is a continuation-in-part of application Ser. No. 090,711 filed Aug. 28, 1987, now abandoned; and, this application is also a continuation-in-part of application Ser. No. 07/537,882 filed Jun. 14, 1990, now U.S. Pat. No. 5,110,587, which in turn is a continuation of U.S. application Ser. No. 07/090,209 filed Aug. 27, 1987, now abandoned, which is a division of U.S. application Ser. No. 622,135 filed Jun. 19, 1984, now U.S. Pat. No. 4,722,848, which in turn is a continuation-in-part of U.S. application Ser. No. 446,824 filed Dec. 8, 1982, now U.S. Pat. No. 4,603,112, which in turn is a continuation-in-part of U.S. application Ser. No. 334,456 filed Dec. 24, 1981, now U.S. Pat. No. 4,769,330.

The present invention relates to methods for inducing an immunological response in vertebrates, including non-avian vertebrates, using synthetic recombinant avipox virus. More particularly, the invention relates to a method for inducing an immunological response in a vertebrate, particularly a mammal, to a vertebrate pathogen by inoculating the vertebrate with a synthetic recombinant avipox virus containing DNA which codes for and expresses the antigenic determinants of said pathogen, and to vaccines comprising such a modified avipox virus. Further, the invention relates to modified avipox virus, to methods for making and using the same, and to certain DNA sequences produced or involved as intermediates in the production of modified avipox virus and to methods for making such sequences.

BACKGROUND OF THE INVENTION

Avipox or avipoxvirus is a genus of closely related pox viruses which infect fowl. The genus avipox includes the species fowlpox, canary pox, junco pox, pigeon pox, quail pox, sparrow pox, starling pox, and turkey pox. The species fowlpox infects chickens, and is not to be confused with the human disease called chickenpox. The genus avipox shares many characteristics with other pox viruses and is a member of the same subfamily, poxviruses of vertebrates, as vaccinia. Pox viruses, including vaccinia and avipox, replicate within eukaryotic host cells. These viruses are distinguished by their large size, complexity, and by the cytoplasmic site of replication. However, vaccinia and avipox are different genera and are dissimilar in their respective molecular weights, their antigenic determinants, and their host species, as reported in Intervirology Vol. 17, pages 42-44, Fourth Report of the International Committee on Taxonomy of Viruses (1982).

The avipox viruses do not productively infect non-avian vertebrates such as mammals, including humans. Further, avipox does not propagate when inoculated into mammalian (including human) cell cultures. In such mammalian cell cultures inoculated with avipox the cells will die because of a cytotoxic effect, but show no evidence of productive viral infection.

The inoculation of a non-avian vertebrate such as a mammal with live avipox results in the formation of a lesion at the inoculation site which resembles a vaccinia inoculation. However, no productive viral infection results. Nevertheless, it has now been found that a mammal so inoculated responds immunologically to the avipox virus. This is an unexpected result.

Vaccines composed of killed pathogen or purified antigenic components of such pathogens must be injected in larger quantities than live virus vaccines to produce an effective immune response. This is because live virus inoculation is a much more efficient method of vaccination. A relatively small inoculum can produce an effective immune response because the antigen of interest is amplified during replication of the virus. From a medical standpoint, live virus vaccines provide immunity that is more effective and longer lasting than does inoculation with a killed pathogen or purified antigen vaccine. Thus, vaccines composed of killed pathogen or purified antigenic components of such pathogens require production of larger quantities of vaccine material than is needed with live virus.

It is clear from the foregoin discussion that there are medical and economic advantages to the use of live virus vaccines. One such live virus vaccine comprises vaccinia virus. This virus is known in the prior art to be a useful one in which to insert DNA representing the genetic sequences of antigens of mammalian pathogens by recombinant DNA methods.

Thus, methods have been developed in the prior art that permit the creation of recombinant vaccinia viruses by the insertion of DNA from any source (e.g. viral, prokaryotic, eukaryotic, synthetic) into a nonessential region of the vaccinia genome, including DNA sequences coding for the antigenic determinants of a pathogenic organism. Certain recombinant vaccinia viruses created by these methods have been used to induce specific immunity in mammals to a variety of mammalian pathogens, all as described in U.S. Pat. No. 4,603,112, incorporated herein by reference.

Unmodified vaccinia virus has a long history of relatively safe and effective use for inoculation against smallpox. However, before the eradication of smallpox, when unmodified vaccinia was widely administered, there was a modest but real risk of complications in the form of generalized vaccinia infection, especially by those suffering from eczema or immunosuppression. Another rare but possible complication that can result from vaccinia inoculation is post vaccination encephalitis. Most of these reactions resulted from inoculating individuals with skin diseases such as eczema or with impaired immune systems, or individuals in households with others who had eczema or impaired immunological responses. Vaccinia is a live virus, and is normally harmless to a healthy individual. However, it can be transmitted between individuals for several weeks after inoculation. If an individual with an impairment of the normal immune response is infected either by inoculation or by contagious transmission from a recently inoculated individual, the consequences can be serious.

Thus, it can be appreciated that a method which confers on the art the advantages of live virus inoculation but which reduces or eliminates the previously discussed problems would be a highly desirable advance over the current state of technology. This is even more important today with the advent of the disease known as acquired immune deficiency syndrome (AIDS). Victims of this disease suffer from severe immunological dysfunction and could easily be harmed by an otherwise safe live virus preparation if they came in contact with such virus either directly or via contact with a person recently immunized with a vaccine comprising such a live virus.

OBJECTS OF THE INVENTION

It is an object of the present invention to provide a vaccine which is capable of immunizing vertebrates against a pathogenic organism, which has the advantages of a live virus vaccine, and which has few or none of the disadvantages of either a live virus vaccine or a killed virus vaccine as enumerated above, particularly when used to immunize non-avian vertebrates.

It is a further object of this invention to provide synthetic recombinant avipox viruses for use in such vaccines.

It is a further object of this invention to provide a method for inducing an immunological response in avian and non-avian vertebrates to an antigen by inoculating the vertebrate with a synthetic recombinant avipox virus which, in the case of non-avian vertebrates such as mammals, cannot productively replicate in the animal with the production of infectious virus. In this case, the virus is self-limiting, reducing the possibility of spreading to non-vaccinated hosts.

It is a still further object of the invention to provide a method for inducing an immunological response in a vertebrate to an antigen, which method comprises inoculating the vertebrate with a vaccine including synthetic recombinant avipox virus which comprises and expresses the antigenic determinant of a pathogen for said vertebrate.

It is another object of the invention to provide a method for expressing a gene product in a vertebrate by inoculating the vertebrate with a recombinant virus containing DNA which codes for and expresses the gene product without productive replication of the virus in the vertebrate.

It is yet another object of the invention to provide a method for inducing an immunological response in a vertebrate to an antigen by inoculating the vertebrate with a recombinant virus containing DNA which codes for and expresses the antigen without productive replication of the virus in the vertebrate.

STATEMENT OF THE INVENTION

In one aspect the present invention relates to a method for inducing an immunological response in a vertebrate to a pathogen by inoculating the vertebrate with a synthetic recombinant avipox virus modified by the presence, in a nonessential region of the avipox genome, of DNA from any source which codes for and expresses an antigen of the pathogen.

In a further aspect, the present invention is directed to a method for expressing a gene product or inducing an immunological response to an antigen in a vertebrate with a recombinant virus which does not productively replicate in the cells of the vertebrate but which does express the gene product or the antigen in those cells.

In another aspect, the present invention is directed to synthetic recombinant avipox virus modified by the insertion therein of DNA from any source, and particularly from a non-avipox source, into a nonessential region of the avipox genome. Synthetically modified avipox virus recombinants carrying exogenous (i.e. non-avipox) genes coding for and expressing an antigen, which recombinants elicit the production by a vertebrate host of immunological responses to the antigen, and therefore to the exogenous pathogen, are used according to the invention to create novel vaccines which avoid the drawbacks of conventional vaccines employing killed or attenuated live organisms, particularly when used to inoculate non-avian vertebrates.

It must be noted again that avipox viruses can only productively replicate in or be passaged through avian species or avian cell lines. The recombinant avipox viruses harvested from avian host cells, when inoculated into a non-avian vertebrate such as a mammal in a manner analogous to the inoculation of mammals by vaccinia virus, produce an inoculation lesion without productive replication of the avipox virus. Despite the failure of the avipox virus to productively replicate in such an inoculated non-avian vertebrate, sufficient expression of the virus occurs so that the inoculated animal responds immunologically to the antigenic determinants of the recombinant avipox virus and also to the antigenic determinants encoded in exogenous genes therein.

When used to inoculate avian species, such a synthetically recombinant avipox virus not only produces an immunological response to antigens encoded by exogenous DNA from any source which may be present therein, but also results in productive replication of the virus in the host with the evocation of an expected immunological response to the avipox vector per se.

Several investigators have proposed creating recombinant fowlpox, specifically viruses for use as veterinary vaccines for the protection of fowl livestock. Boyle and Coupar, J. Gen. Virol. 67, 1591-1600 (1986), and Binns et al., Isr. J. Vet. Med. 42, 124-127 (1986). Neither proposals nor actual reports directed to the use of recombinant avipox viruses as a method to induce specific immunity in mammals have been uncovered.

Stickl and Mayr, Fortschr. Med. 97(40), pages 1781-1788 (1979) describe the injection of avipox, specifically fowlpox, virus into humans. However, these studies relate only to the use of ordinary fowlpox to enhance nonspecific immunity in patients suffering from the after effects of cancer chemotherapy. No recombinant DNA techniques are employed. There is no teaching of an avipox into which DNA coding for antigens of vertebrate pathogens had been inserted, or of a method for inducing specific immunity in vertebrates. Instead, the prior art depended upon a general and nonspecific tonic effect on the human host.

A more complete discussion of the basis of genetic recombination may help in understanding how the modified recombinant viruses of the present invention are created.

Genetic recombination is in general the exchange of homologous sections of deoxyribonucleic acid (DNA) between two strands of DNA. (In certain viruses ribonucleic acid [RNA] may replace DNA). Homologous sections of nucleic acid are sections of nucleic acid (RNA or DNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene.

Successful expression of the inserted DNA genetic sequence by the modified infectious virus requires two conditions.

First, the insertion must be into a nonessential region of the virus in order that the modified virus remain viable. Neither fowlpox nor the other avipox viruses have as yet demonstrated nonessential regions analogous to those described for the vaccinia virus. Accordingly, for the present invention nonessential regions of fowlpox were discovered by cleaving the fowlpox genome into fragments, then separating the fragments by size and inserting these fragments into plasmid constructs for amplification. (Plasmids are small circular DNA molecules found as extra chromosomal elements in many bacteria including *E. coli*. Methods for inserting DNA sequences such as the genes for antigenic determinants or other genetic markers into plasmids are well known to the art and described in detail in Maniatis et al., *Molecular Cloning: A Laboratory Manual*, Cold Spring Harbor Laboratory New York [1982]). This was followed by insertion of genetic markers and/or genes coding for antigens into the cloned fowlpox fragments. Those fragments which directed successful recombination, as proved by successful recovery of the genetic marker or antigens, were those which comprised DNA inserted into a nonessential region of the fowlpox genome.

The second condition for expression of inserted DNA is the presence of a promoter in the proper relationship to the inserted DNA. The promoter must be placed so that it is located upstream from the DNA sequence to be expressed. Because avipox viruses are not well characterized and avipox promoters have not previously been identified in the art, known promoters from other pox viruses are usefully inserted upstream of the DNA to be expressed as part of the present invention. Fowlpox promoters also can be successfully used to carry out the methods and make the products of the invention. According to the present invention, fowlpox promoters, vaccinia promoters and entomopox promoters have been found to promote transcription in recombinant pox virus.

Boyle and Coupar, J. gen. Virol. 67, 1591, (1986) have published speculation that vaccinia promoters "might be expected to operate in (fowlpox) virus." The authors located and cloned a fowlpox TK gene (Boyle et al., Virology 156, 355-365 [1987]) and inserted it into a vaccinia virus. This TK gene was expressed, presumably because of recognition of the fowlpox TK promoter sequence by vaccinia polymerase functions. However, despite their speculation, the authors did not insert any vaccinia promoter into a fowlpox virus nor observe any expression of a foreign DNA sequence present in a fowlpox genome. It was not known before the present invention that promoters from other pox viruses, such as vaccinia promoters, would in fact promote a gene in an avipox genome.

DESCRIPTION OF CERTAIN PREFERRED EMBODIMENTS

Fowlpox and canarypox viruses have been particularly used according to the present invention as preferred avipox species to be modified by recombination in incorporating exogenous DNA thereinto.

Fowlpox is a species of avipox which infects chickens in particular, but does not infect mammals. The fowlpox strain designated herein as FP-5 is a commercial fowlpox virus vaccine strain of chicken embryo origin available from American Scientific Laboratories (Division of Schering Corp.) Madison, Wis., United States Veterinary License No. 165, Serial No. 30321.

The fowlpox strain designated herein as FP-1 is a Duvette strain modified to be used as a vaccine in one-day old chickens. The strain is a commercial fowlpox virus vaccine strain designated O DCEP 25/ CEP67/ 2309 October 1980 and is available from Institute Merieux, Inc.

Canarypox is another species of avipox. Analogously to fowlpox, canarypox particularly infects canaries, but does not infect mammals. The canarypox strain designated herein as CP is a commercial canarypox vaccine strain designated LF2 CEP 524 24 10 75 and is available from Institute Merieux, Inc.

The DNA genetic sequences inserted into these avipox viruses by genetic recombination according to the present invention include the Lac Z gene, of prokaryotic origin; the rabies glycoprotein (G) gene, an antigen of a non-avian (specifically mammalian) pathogen; the turkey influenza hemagglutinin gene, the antigen of a pathogenic avian virus other than an avipox virus; the gp51,30 envelope gene of the bovine leukemia virus, a mammalian virus; the fusion protein gene of the Newcastle disease virus (Texas strain), an avian virus; the FeLV envelope gene of the feline leukemia virus, a mammalian virus; the RAV-1 env gene of the rous associated virus which is an avian virus/poultry disease; the nucleoprotein (NP) gene of the Chicken/Pennsylvania/1/83 influenza virus, an avian virus; the matrix gene and peplomer gene of the infectious bronchitis virus (strain Mass 41), an avian virus; and the glycoprotein D gene (gD) of herpes simplex virus, a mammalian virus.

Isolation of the Lac Z gene is described by Casadaban et al., Methods in Enzymology 100, 293-308 (1983). The structure of the rabies G gene is disclosed, for example, by Anilionis et al., Nature 294, 275-278 (1981).

Its incorporation into vaccinia and expression in this vector are discussed by Kieny et al., Nature 312, 163-166 (1984). The turkey influenza hemagglutinin gene is described by Kawaoka et al., Virology 158, 218-227 (1987). The bovine leukemia virus gp51,30 env gene has been described by Rice et al., Virology 138, 82-93 (1984). The fusion gene of the Newcastle disease virus (Texas strain) is available from Institute Merieux, Inc., as plasmid pNDV 108. The feline leukemia virus env gene has been described by Guilhot et al., Virology 161, 252-258 (1987). The rous associated virus type 1 is available from Institute Merieux, Inc., as two clones, penVRVIPT and mp19env (190). Chicken influenza NP gene is available from Yoshihiro Kawaoka of St. Jude Children's Research Hospital as plasmid pNP 33. An infectious bronchitis virus cDNA clone of the IBV Mass 41 matrix gene and peplomer gene are available from Institute Merieux, Inc. as plasmid pIBVM63. The herpes simplex virus gD gene is described in Watson et al., Science 218, 381–384 (1982).

The recombinant avipox viruses described in more detail below incorporate one of three vaccinia promoters. The Pi promoter, from the Ava I H region of vaccinia, is described in Wachsman et al., J. of Inf. Dis. 155, 1188–1197 (1987). More in particular, this promoter is derived from the Ava I H(Xho I G) fragment of the L-variant WR vaccinia strain, in which the promoter directs transcription from right to left. The map location of the promoter is approximately 1.3 Kbp (kilobase pair) from the left end of Ava IH, approximately 12.5 Kbp from the left end of the vaccinia genome, and about 8.5 Kbp left of the Hind III C/N junction. The sequence of the promoter is:

```
(GGATCCC)-ACTGTAAAAATAGAAAC-
TATAATCATATAATAGTGTAGGTTG-
GTAGTA
GGGTACTCGTGATTAATTTTATTGT-
TAAACTTG-(AATTC).
``` wherein the symbols in parentheses are linker sequences.

The Hind III H promoter (also "HH" and "H6" herein) was defined by standard transcriptional mapping techniques. It has the sequence

```
ATTCTTTATTCTATACTTAAAAAATGAAAA
TAAATACAAAGGTTCTTGAGGGTTGTGTTAAATTGAAAGCGAGAAATAATCATAAATT
ATTTCATTATCGCGATATCCGT
TAAGTTTGTATCGTAATG.
```

The sequence is identical with that described as being upstream of open reading frame H6 by Rosel et al., J. Virol. 60, 436–449 (1986).

The 11K promoter is as described by Wittek, J. Virol. 49, 371–378 (1984) and Bertholet, C. et al., Proc. Natl. Acad. Sci. USA 82, 2096–2100 (1985).

The recombinant avipox viruses of the present invention are constructed in two steps known in the art and analogous to those disclosed in aforementioned U.S. Pat. No. 4,603,112 for creating synthetic recombinants of the vaccinia virus.

First, the DNA gene sequence to be inserted into the virus is placed into an E. coli plasmid construct into which DNA homologous to a section of nonessential DNA of the avipox virus has been inserted. Separately, the DNA gene sequence to be inserted is ligated to a promoter. The promoter-gene linkage is then inserted into the plasmid construct so that the promoter-gene linkage is flanked on both ends by DNA homologous to a nonessential region of avipox DNA. The resulting plasmid construct is then amplified by growth within E. coli bacteria. (Plasmid DNA is used to carry and amplify exogenous genetic material, and this method is well known in the art. For example, these plasmid techniques are described by Clewell, J. Bacteriol. 110, 667–676 (1972). The techniques of isolating the amplified plasmid from the E. coli host are also well known in the art and are described, for instance, by Clewell et al. in Proc. Natl. Acad. Sci. U.S.A. 62, 1159–1166 (1969).)

The amplified plasmid material isolated after growth within E. coli is then used for the second step. Namely, the plasmid containing the DNA gene sequence to be inserted is transfected into a cell culture, e.g. chick embryo fibroblasts, along with the avipox virus (such as fowlpox strain FP-1 or FP-5). Recombination between homologous fowlpox DNA in the plasmid and the viral genome respectively gives an avipox virus modified by the presence, in a nonessential region of its genome, of non-fowlpox DNA sequences.

A better understanding of the present invention and of its many advantages will be had from the following examples, given by way of illustration.

EXAMPLE 1

Transient Expression Assays Demonstrating Recognition of Vaccinia Promoters by Fowlpox RNA Transcription Factors A number of plasmid constructions were made containing the Hepatitis B virus surface antigen (HBSAg) coding sequence linked to vaccinia virus promoter sequences. Fifty ug of each plasmid were transfected onto CEF cells infected with 10 pfu per cell of fowlpox virus or vaccinia virus. Infection was allowed to proceed for 24 hours and cells were then lysed by three successive cycles of freezing and thawing.

The amount of HBSAg in the lysate was estimated using the commerically available AUSRIA II-$^{125}$I kit from Abbott Laboratories, Diagnostic Division. The presence or absence of HBSAg is expressed as a ratio of the net counts (sample minus background) of the unknown to a negative cutoff value pre-determined by the manufacturer. This results in a P/N (positive/negative) ratio. The results are shown in Table I.

Three different vaccinia promoter sequences were used: the Pi promoter, recognized early in vaccinia infection before DNA replication; the 11K promoter, recognized late in vaccinia infection after the onset of DNA replication; and the Hind III H (HH) promoter, recognized both early and late in vaccinia infection. These promoters are described earlier herein.

The data indicate that HBSAg produced in the lysates of infected cells is the result of recognition of vaccinia promoters by either fowlpox or vaccinia transcriptional factors.

TABLE I

| Plasmid | Virus | Description | P/N Ratio |
| --- | --- | --- | --- |
| pMP 131piR$_2$ | Fowlpox | SAg linked to | 1.8 |
|  | Vaccinia | Pi promoter | 9.1 |
| pMPK 22.13S | Fowlpox | SAg linked to | 14 |
|  | Vaccinia | 11K promoter | 2 |
| pPDK 22.5 | Fowlpox | SAg linked to | 92.6 |
|  | Vaccinia | 11K promoter | 5.6 |
| pRW 668 | Fowlpox | SAg linked to | 77 |
|  | Vaccinia | HH promoter | 51.4 |
| (no plasmid) | Fowlpox |  | 1.1 |
| (no plasmid) | Vaccinia |  | 1.3 |
| pMPK 22.13S | (no virus) |  | 1.3 |

EXAMPLE 2

Construction of Recombinant Fowlpox Virus vFP-1 Containing the LAC Z Gene

A fragment in a nonessential region of the fowlpox virus was located and isolated as follows.

The nuclease Bal 31 was employed to remove the single stranded terminal hairpin loops of FP-5 DNA. The Klenow (large) fragment of DNA polymerase I was used to create blunt ends. Following removal of the loops, the fragments were generated by restriction endonuclease digestion with Bgl II. This digestion produced a series of FP-5 fragments which were separated by agarose gel electrophoresis.

An 8.8 Kbp BglII blunt ended fragment was isolated and ligated into a commercially available plasmid, pUC 9, which had been cleaved with Bam HI and Sma I. The resulting plasmid was designated pRW 698.

To decrease the size of the fowlpox fragment, this plasmid was cleaved with Hind III to create two further fragments. A 6.7 Kbp fragment was discarded and the remaining 4.7 Kbp fragment was ligated onto itself to form a new plasmid designated pRW 699.

To incorporate an 11K promoted Lac Z gene into this plasmid, pRW 699 was cut with EcoRV, which cleaves the plasmid at only one site. The 11K promoted Lac Z segment was then inserted as a blunt ended PstI-Bam HI fragment, creating a new plasmid designated pRW 702. The Lac Z clone is from pMC 1871, as described in Casadaban et al., loc. cit. The 11K promoter was ligated to the eighth codon of the Lac Z gene via a Bam HI linker.

With recombination techniques like those taught for vaccinia in U.S. Pat. No. 4,603,112, the pRW 702 plasmid was then recombined with the fowlpox virus FP-5 growing on chick embryo fibroblasts (CEF) using the following procedures to generate vFP-1. Fifty ug of pRW 702 DNA was mixed in a final volume of 100 ul with 0.5 ug of whole genome fowlpox DNA. To this were added 10 ul of 2.5M $CaCl_2$ and 110 ul of $2 \times$ HEBS buffer (pH 7) prepared from:

40 mM Hepes
300 mM NaCl
1.4 mM $Na_2HPO_4$
10 mM KCl
12 mM dextrose.

After 30 minutes at room temperature, 200 ul of a fowlpox virus pool diluted to give 5 pfu/cell were added and the mixture inoculated onto 60 mm dishes containing a primary CEF monolayer. 0.7 ml of Eagles medium containing 2% fetal bovine serum (FBS) was also added at this time. The plates were incubated at 37° C. for 2 hours, after which an additional 3 ml of Eagles medium containing 2% FBS was added and the plates incubated for 3 days. Cells were lysed by three successive cycles of freezing and thawing and progeny virus was then assayed for the presence of recombinants.

Proof of successful insertion by recombination of the 11K-promoted Lac Z gene into the genome of fowlpox FP-5 was obtained by testing for expression of the Lac Z gene. The Lac Z gene codes for the enzyme Beta-galactosidase, which cleaves the chromogenic substrate 5-bromo-4-chloro-3-indolyl-Beta-D-galactoside (X-gal) releasing a blue indolyl derivative. Blue plaques were selected as positive recombinants.

The successful insertion of Lac Z into the genome of fowlpox FP-5 and its expression were also confirmed by immune precipitation of the Beta-galactosidase protein with commercially available antisera and standard techniques using vFP-1 infected CEF, BSC (monkey kidney cell line-ATCC CCL26) and VERO (monkey kidney cell line-ATCC CCL81).

The expression of Beta-galactosidase by the recombinant virus vFP-1 was further confirmed in vivo by inoculating rabbits and mice with the virus and successfully measuring a post-inoculation rise in the titers of antibodies directed against the Beta-galactosidase protein in the serum of the inoculated animals.

In particular, the recombinant vFP-1 was purified from host cell contaminants and inoculated intradermally at two sites on each side of two rabbits. Each rabbit received a total of $10^8$ pfu.

Animals were bled at weekly intervals and the sera used in an ELISA assay using a commercially available preparation of purified Beta-galactosidase as an antigen source.

Both rabbits and mice inoculated with the recombinant vFP-1 produced an immune response to the Beta-galactosidase protein as detected in an ELISA assay. In both species the response was detectable by one week post-inoculation.

EXAMPLE 3

Construction from Fowlpox Virus FP-5 of the Recombinant Virus vFP-2 Containing the Rabies G Gene and Lac Z A 0.9 Kbp Pvu II fragment was obtained from FP-5 and inserted by standard techniques between the two Pvu II sites in pUC 9. The resulting construct, designated pRW 688.2, has two Hinc II sites, approximately 30 bp apart, asymmetric within the Pvu II fragment and thus forming a long arm and a short arm of the fragment.

Oligonucleotide adapters were inserted between these Hinc II sites using known techniques to introduce Pst I and Bam HI sites, thus creating plasmid pRW 694.

This plasmid was now cleaved with Pst I and Bam HI and the Lac Z gene having a linked 11K vaccinia promoter described earlier was inserted to create the new plasmid pRW 700.

To create a Pi-promoted rabies G gene, the Bgl II site which is 5'-proximal to the rabies gene (cf. Kieny et al., loc. cit.) was blunt ended and ligated to the filled-in Eco RI site of the Pi promoter described earlier.

This construct was inserted at the Pst I site of pRW 700 to create plasmid pRW 735.1 having therein the foreign gene sequence Pi-rabies G-11K-Lac Z. This insert is so oriented within the plasmid that the long Pvu II-Hinc II arm of the FP-5 donor sequence is 3' to the Lac Z gene.

The resulting final construct was recombined with fowlpox virus FP-5 by infection/transfection of chick embryo fibroblasts by the methods previously described to create recombinant fowlpox virus vFP-2. This recombinant virus was selected by X-gal staining.

The proper insertion and expression of both the Lac Z marker gene and the rabies G gene were verified by a number of additional methods described below.

Immunofluorescent localization of the rabies antigen by specific antibodies successfully demonstrated rabies antigen expression on the surface of avian and non-avian cells infected with vFP-2 virus.

As earlier, the expression of rabies antigen and Beta-galactosidase by avian and non-avian cells infected with the vFP-2 virus was confirmed by the immune precipitation method.

Further proof that the vFP-2 embodiment of this invention is a successful recombinant virus carrying the genes for rabies G and Beta-galactosidase was obtained by inoculating two rabbits with vFP-2 virus. Both rabbits were inoculated intradermally with $1\times10^8$ pfu per rabbit of vFP-2. Both of these rabbits produced typical pox lesions. The rabbits were bled at weekly intervals and sera were tested by ELISA to detect the presence of antibody specific for the rabies glycoprotein and the Beta-galactosidase protein.

As reported in Table II below, rabbit 205 showed detectable levels of anti-Beta-galactosidase antibody by the ELISA test at one week post-inoculation. This rose at two weeks to a titer of 1 in 4000 which was maintained to five weeks post inoculation. Using the antigen capture ELISA assay, sera from rabbit 205 showed detectable levels of anti-rabies antibodies from 3 to 10 weeks post-inoculation.

TABLE II

Antibody Production by Rabbit 205 Against Rabies Antigen and Beta-Galactosidase Protein

| Time | Antibody Titer (Reciprocal of Serum Dilution) |
|---|---|
| Prebleed anti-B-galactosidase | 0 |
| Week 1 | 500 |
| Weeks 2-5 (each) | 4000 |
| Week 6 | 500 |
| Week 9 | 250 |
| Prebleed anti-rabies | 0 |
| Week 3 | 200 |
| Week 6 | 200 |
| Week 10 | 100 |

EXAMPLE 4A

Construction from Fowlpox Virus FP-1 of Recombinant Virus vFP-3 Containing Promoted Rabies G Gene This embodiment demonstrates that the rabies G gene is fully expressed by fowlpox strains other than FP-5, specifically by another strain of fowlpox virus designated FP-1.

As in Example 3, a 0.9 Kbp Pvu II fragment was obtained from FP-1 on the assumption that, as in FP-5, the fragment would contain a nonessential region.

This fragment was inserted between the two Pvu II sites of pUC 9, generating a plasmid designated pRW 731.15R.

This plasmid has two Hinc II sites, approximately 30 bp apart, asymmetric within the Pvu II fragment and thus forming a long arm and a short arm of the fragment.

A commercially available Pst linker (5')-CCTGCAGG-(3')

was inserted between the two Hinc II sites creating plasmid pRW 741.

An HH-promoted rabies G gene was inserted into this plasmid at the Pst I site, to generate the new plasmid pRW 742B. By recombination of this plasmid with FP-1 by infection/transfection of CEF cells, virus vFP-3 was obtained.

The ATG translational initiation codon of the open reading frame promoted by the HH promoter was superimposed on the initiation codon of the rabies G gene using a synthetic oligonucleotide spanning the EcoRV site in the HH promoter and the Hind III site in the rabies G gene.

The 5' end of this HH-promoted rabies gene was modified by known techniques to contain a Pst I site and the construct was then ligated into the Pst I site of pRW 741 to create pRW 742B. The orientation of the construct in the plasmid is the same as in pRW 735.1 discussed earlier in Example 3.

Recombination was carried out as described in Example 2. The resulting recombinant is called vFP-3.

The expression of rabies antigen by both avian and non-avian cells infected with the vFP-3 virus was confirmed by the immune precipitation and immunofluorescence techniques earlier described.

Further proof that the vFP-3 embodiment of this invention is a successful recombinant virus expressing the genes for rabies G was obtained by intradermally inoculating pairs of rabbits with the recombinant virus. Two rabbits were inoculated intradermally with $1 \times 10^8$ pfu of vFP-3 per rabbit. Both of these rabbits produced typical pox lesions reaching maximum size 5-6 days post-inoculation. The rabbits were bled at weekly intervals and sera were tested by ELISA to detect the presence of antibody specific for the rabies glycoprotein.

Each of five rats was also inoculated intradermally with $5 \times 10^7$ pfu of vFP-3. Lesions resulted in all animals.

Both rabbits and rats produced detectable levels of antibody specific to rabies by two weeks after inoculation. Two control rabbits inoculated intradermally with the parental FP-1 virus had no detectable levels of anti-rabies antibody.

To exclude the possibility that the antibody response was due to the introduction of rabies antigen adventitiously carried with the inoculum virus or integrated into the membrane of the recombinant fowlpox virus, rather than being caused by de novo synthesis of the rabies antigen by the recombinant virus in the animal as proposed, the vFP-3 virus was chemically inactivated and inoculated into rabbits.

The purified virus was inactivated overnight at 4° C. in the presence of 0.001% of beta propiolactone and then pelleted by centrifugation. The pelleted virus was collected in 10 mM Tris buffered saline, sonicated, and titrated to assure that no infectious virus remained. Two rabbits were inoculated intradermally with inactivated vFP-3 and two with an equivalent amount of untreated recombinant. Lesion sizes were monitored.

Both rabbits receiving untreated vFP-3 developed typical pox lesions graded as 4-5+ at 5 days post-inoculation. Rabbits inoculated with inactivated virus also developed lesions, but these were graded as 2+ at 5 days post-inoculation.

Rabbits were bled at weekly intervals and the sera tested by ELISA for the presence of rabies specific antibody and fowlpox specific antibodies. The results are shown in Table III below.

TABLE III

| | Live vFP-3 | | | | Inactivated vFP-3 | | | |
|---|---|---|---|---|---|---|---|---|
| | Rabbit: | | | | | | | |
| | No. 295 | | No. 318 | | No. 303 | | No. 320 | |
| | Antibody Tested: | | | | | | | |
| Week P.I | Rabies | FP | Rabies | FP | Rabies | FP | Rabies | FP |
| 0 | 0 | 0 | 0 | 0 | 0 | 0 | 0 | 0 |
| 2 | 250 | 4000 | 500 | 4000 | 0 | 50 | 0 | 1000 |
| 3 | 1000 | 4000 | 500 | 4000 | 0 | 4000 | 0 | 2000 |
| 4 | 1000 | 4000 | 2000 | 4000 | 0 | 4000 | 0 | 2000 |
| 5 | 4000 | 4000 | 2000 | 4000 | 0 | 2000 | 0 | 4000 |
| 6 | 4000 | 4000 | 4000 | 4000 | 0 | 2000 | 0 | 2000 |

In this test the titer end point (expressed as the reciprocal of the serum dilution) was arbitrarily set at 0.2 after the absorbance values of all pre-challenge sera were subtracted. Both rabbits 295 and 318 receiving the live virus developed an immune response to the rabies glycoprotein and to fowlpox virus antigens. Rabbits 303 and 320 also developed an immune response to fowlpox virus antigens although the titer was lower. Neither of these rabbits developed a detectable response to the rabies glycoprotein.

This finding signifies that the immune response produced in the rabbit is due to the de novo expression of the rabies glycoprotein gene carried in the recombinant virus and is not a response to any adventitious glycoprotein carried in the inoculum virus.

EXAMPLE 4B

Construction from Fowlpox Virus FP-1 of the Recombinant Virus vFP-5 Containing Unpromoted Rabies G Gene Expression of a foreign gene inserted by recombination into the fowlpox genome requires the presence of a promoter. This was demonstrated by the creation of a further recombinant, vFP-5, identical to vFP-3 except for the omission of the HH promoter. The presence of the rabies gene in this recombinant was confirmed by nucleic acid hybridization. However, no rabies antigen was detected in CEF cell cultures infected by the virus.

EXAMPLE 5

In vitro Passaging Experiments to Determine whether Fowlpox Virus Replicates in Non-Avian Cells An experiment was performed in which three cell systems, one avian and two non-avian, were inoculated with the parental FP-1 strain or the recombinant vFP-3. Two dishes each of CEF, MRC-5, and VERO, respectively, were inoculated with FP-1 or vFP-3 at an input multiplicity of 10 pfu per cell.

At three days, one dish each was harvested. The virus was released by three successive cycles of freezing and thawing and re-inoculated onto a fresh monolayer of the same cell line. This was repeated for six sequential passages and, at the end of the experiment, samples of each passage were titrated for virus infectivity on CEF monolayers.

The results are shown in Table IVA and indicate that the serial passage of both FP-1 and vFP-3 is possible in CEF cells but not in either of the two non-avian cells lines. Infectious virus is not detectable after 3 or 4 passages in VERO or MRC-5 cells.

The second dish was used to determine if virus, not detectable by direct titration, could be detected after amplification in the permissive CEF cells. At three days, cells on the second dish were harvested by scraping and a third of the cells lysed and inoculated onto a fresh CEF monolayer. When full cytopathic effect (CPE) was reached or at 7 days post-infection, the cells were lysed and the virus yield titrated. The results are shown in Table IVB. When passage in CEF cells was used to amplify any virus present, the virus could not be detected after four or five passages.

Attempts to establish persistently infected cells failed.

In a further attempt to detect evidence of continued viral expression in non-avian cells, the samples used for viral titration above were used in a standard immunodot assay in which anti-fowlpox antibody and anti-rabies antibody were used to detect the presence of the respective antigens. The results of these assays confirm the titration results.

TABLE IVA

| Inoculum Virus Cell Type | Passaging Experiment | | | | | |
|---|---|---|---|---|---|---|
| | FP-1 | | | vFP-3 | | |
| | CEF | VERO | MRC-5 | CEF | VERO | MRC-5 |
| Pass | | | | | | |
| 1 | 6.6$^a$ | 4.8 | 4.9 | 6.6 | 5.4 | 6.2 |
| 2 | 6.7 | 2.9 | 3.7 | 6.5 | 4.2 | 5.1 |
| 3 | 6.4 | 1.4 | 1.0 | 6.4 | 1.7 | 4.4 |
| 4 | 6.1 | N.D$^b$ | N.D | 6.2 | N.D | 1.0 |
| 5 | 6.4 | N.D | N.D | 6.3 | N.D | N.D |
| 6 | 5.7 | N.D | N.D | 5.9 | N.D | N.D |

$^a$titer of virus expressed as $\log_{10}$ pfu per ml.
$^b$not detectable.

TABLE IVB

| Inoculum Virus Cell Type | Amplification Experiment | | | | | |
|---|---|---|---|---|---|---|
| | FP-1 | | | vFP-3 | | |
| | CEF | VERO | MRC-5 | CEF | VERO | MRC-5 |
| Pass | | | | | | |
| 1 | 6.4$^a$ | 6.2 | 6.4 | 6.5 | 6.3 | 6.4 |
| 2 | 7.5 | 6.3 | 6.0 | 6.5 | 6.3 | 5.5 |
| 3 | 6.2 | 6.7 | 5.3 | 5.9 | 6.1 | 6.3 |
| 4 | 5.6 | 4.6 | 3.9 | 5.7 | 4.8 | 5.8 |
| 5 | 6.3 | 4.1 | N.D | 6.1 | 4.7 | 4.7 |
| 6 | 6.2 | N.D$^b$ | N.D | 6.2 | N.D | N.D |

$^a$titer of virus expressed as $\log_{10}$ pfu per ml.
$^b$not detectable.

EXAMPLE 6

Additional Recombinants of Fowlpox FP-1: vFP-6, vFP-7, vFP-8, and vFP-9

Recombinant viruses vFP-6 and vFP-7 were constructed by the following procedure.

A 5.5 Kbp Pvu II fragment of FP-1 was inserted between the two Pvu II sites in pUC 9 to create the plasmid pRW 731.13. This plasmid was then cut at a unique Hinc II site and blunt ended HH-promoted rabies G gene inserted to create plasmids pRW 748A and B, representing opposite orientations of the insert. Plasmids pRW 748A and B were then used separately to transfect CEF cells along with FP-1 virus to produce vFP-6 and vFP-7, respectively, by recombination. This locus is now designated as locus f7.

A 10 Kbp Pvu-II fragment of FP-1 was inserted between the two Pvu II sites of pUC 9 to create pRW 731.15. This plasmid was then cut at a unique Bam HI site and then an 11K promoted Lac Z gene fragment was inserted, generating pRW 749A and B, representing opposite orientations of the insert. Recombination of these donor plasmids with FP-1 resulted in vFP-8 and vFP-9, respectively. This locus is now designated as locus f8.

vFP-8 and vFP-9 expressed the Lac Z gene as detected by X-gal. vFP-6 and vFP-7 expressed the rabies G gene as detected by rabies-specific antiserum.

EXAMPLE 7

Immunization with vFP-3 to Protect Animals against Challenge with Live Rabies Virus Groups of 20 female SPF mice, 4-6 weeks, were inoculated with 50 ul of vFP-3 in the footpad in doses ranging from 0.7 to 6.7 TCID$_{50}$ per mouse. (The TCID$_{50}$ or tissue culture infectious dose is that dose at which 50 percent of tissue culture cells suffer cytopathic effect). At 14 days post-vaccination 10 mice in each group were sacrificed and serum samples collected for assay in the RFFI test. The remaining 10 mice were challenged by inoculation of 10 $LD_{50}$ of CVS strain rabies by the intracerebral route and survivors calculated at 14 days post-challenge.

The results are shown in Table VA below.

TABLE VA

| Dose vFP-3 $Log_{10}$ $TCID_{50}$ | Rabies Antibody Titer $Log_{10}$ Dilution* | Survival |
|---|---|---|
| 6.7 | 1.9 | 8/10 |
| 4.7 | 1.8 | 0/10 |
| 2.7 | 0.4 | 0/10 |
| 0.7 | 0.4 | 0/10 |

*As measured in the RFFI (Rapid Fluorescent Focus Inhibition) test. Laboratory Techniques in Rabies, Third Ed., 354-357, WHO Geneva.

The experiment was repeated with 12.5 $LD_{50}$ of challenge rabies virus. The results are shown in Table VB below.

TABLE VB

| Dose vFP-3 $Log_{10}$ $TCID_{50}$ | Rabies Antibody Titer $Log_{10}$ Dilution* | Survival |
|---|---|---|
| 6.7 | 2.8 | 5/10 |
| 4.7 | 2.1 | 2/10 |
| 2.7 | 0.6 | 0/8 |
| 0.7 | 0.6 | 0/8 |

Two dogs and two cats were immunized with a single subcutaneous inoculation of 8 $log_{10}$ $TCID_{50}$ of the recombinant vFP-3. In addition, two dogs and four cats of equivalent age and weight were held as non-vaccinated controls. All animals were bled at weekly intervals. At day 94 each dog was challenged by inoculation in the temporal muscle with two doses of 0.5 ml of a salivary gland homogenate of the NY strain of rabies virus available from Institut Merieux, Inc. The total dose corresponded to 10,000 mouse $LD_{50}$ by an intracerebral route. The six cats were similarly challenged by inoculation in the neck muscle with two doses of 0.5 ml of the same virus suspension. The total dose per animal corresponded to 40,000 mouse $LD_{50}$ by an intracerebral route. The animals were observed daily. All non-vaccinated animals died on the day indicated in Table VI with rabies symptoms. The vaccinated animals survived challenge and were observed for three weeks after the death of the last control animal. The results are shown in Table VI below.

TABLE VI

| | | Titer at Days post-Inoculation | | | | | Survival/ |
|---|---|---|---|---|---|---|---|
| Animal | Vaccination | 0 | 14 | 21 | 28 | 94 | Time of Death |
| Cat | | | | | | | |
| 7015 | vFP-3[a] | 0 | 2.2[b] | 2.4 | 2.4 | 1.5 | + |
| 7016 | vFP-3 | 0 | 1.7 | 1.9 | 2.0 | 1.3 | + |
| 8271 | c[c] | 0 | 0 | 0 | 0 | 0 | d/13[d] |
| T10 | c | 0 | 0 | 0 | 0 | 0 | d/12 |
| T41 | c | 0 | 0 | 0 | 0 | 0 | d/13 |
| T42 | c | 0 | 0 | 0 | 0 | 0 | d/12 |
| Dog | | | | | | | |
| 426 | vFP-3 | 0 | 0.8 | 1.0 | 1.1 | 1.2 | + |
| 427 | vFP-3 | 0 | 1.5 | 2.3 | 2.2 | 1.9 | + |
| 55 | c | 0 | 0 | 0 | 0 | 0 | d/15 |
| 8240 | c | 0 | 0 | 0 | 0 | 0 | d/16 |

[a]Both cats and dogs vaccinated with vFP-3 received 8 $log_{10}$ $TCID_{50}$ by the subcutaneous route.
[b]Titer expressed as $log_{10}$ highest serum dilution giving greater than 50% reduction in the number of fluorescing wells in an RFFI test.
[c]Non-vaccinated control animals.
[d]Animal died/day of death post-challenge.

In further experiments, the recombinant viruses vFP-2 and vFP-3 were inoculated into cattle by several different routes.

Inoculated animals were tested for anti-rabies antibody at days 6, 14, 21, 28, and 35. As shown in following Table VIIA, all animals showed a serological response to the rabies antigen.

TABLE VIIA

Antibody Titers in Mammals Inoculated with vFP-3
Anti-rabies Neutralizing Antibodies
RFFI Test $Log_{10}$ Dilut.

| | Day | | | | | |
|---|---|---|---|---|---|---|
| Cattle No. | 0 | 6 | 14 | 21 | 28 | 35 |
| 7.3 $log_{10}$ $TCID_{50}$ 1420 (intraderm) | NEG | 0.6 | 2 | 1.7 | 1.8 | 1.7 |
| 8 $log_{10}$ $TCID_{50}$ 1419 (subcut) | NEG | 1.6 | 2.2 | 2.1 | 2.1 | 1.9 |
| 8 $log_{10}$ $TCID_{50}$ 1421 (intramusc) | NEG | 0.9 | 2.2 | 2.2 | 1.8 | 1.7 |
| 7.3 $log_{10}$ $TCID_{50}$ 1423 (intramusc) | NEG | 0.9 | 1.1+ | 1+ | 1+ | 1.1+ |

– Not significant

All the cattle were revaccinated with 8 $log_{10}$ $TCID_{50}$ at day 55 post-inoculation and exhibited an anamnestic response to the rabies antigen. In the booster revaccination, all cattle were inoculated subcutaneously except No. 1421, which was again inoculated intramuscularly. RFFI titers were determined on days 55, 57, 63, 70, 77, and 86. The results are shown in Table VIIB.

TABLE VIIB

| | Day | | | | | |
|---|---|---|---|---|---|---|
| Cattle No. | 55 | 57 | 63 | 70 | 77 | 86 |
| 1419 | 1.7 | 1.5 | 2.9 | 2.9 | 2.6 | 2.9 |
| 1420 | 1.0 | 0.5 | 1.9 | 2.3 | 2.2 | 2.0 |
| 1421 | 1.3 | 1.2 | 2.9 | 2.7 | 2.5 | 2.5 |
| 1423 | 1.0 | 0.7 | 2.4 | 2.5 | 2.5 | 2.2 |

All data are for vFP-3 except for animal 1423, which is for vFP-2.

Cattle, cats, and rabbits were also inoculated intradermally with known amounts of fowlpox virus and scabs were collected from the animals after about a week. These were ground, suspended in saline, and titrated to determine virus levels.

Only residual amounts of infectious virus could be recovered. This demonstrates that no productive infection occurred in vivo.

EXAMPLE 8

Inoculation of Chickens with vFP-3

The recombinant fowlpox virus vFP-3 was inoculated into chickens to demonstrate the expression of foreign DNA by a recombinant fowlpox virus in a system permitting productive replication of the vector.

White leghorn chickens were inoculated intramuscularly with 9 $log_{10}$ $TCID_{50}$ vFP-3 or 3 $log_{10}$ $TCID_{50}$ vFP-3 by wing transfixion. Blood samples were taken for an RFFI test for rabies antibody titer 21 days after vaccination. Day 21 titers in inoculated chickens were significantly higher than day 21 titers in controls. Namely, the average titer in the uninfected controls was 0.6; the average in the intramuscularly inoculated birds was 1.9; that in the transfixed birds was 1.2.

EXAMPLE 9

Recombinant Fowlpox vFP-11 Expressing Turkey Influenza H5 HA Antigen

Avian species can be immunized against avian pathogens using the recombinant avipox viruses of the invention.

Thus, novel plasmid pRW 759 (described below), derived from fowlpox virus FP-1 and containing the Hind III H-promoted hemagglutinin gene (H5) of A/turkey/Ireland/1378/83 (TYHA), was used to transfect CEF cells concurrently infected with parent virus FP-1. Recombinant fowlpox virus vFP-11 was obtained by the techniques described earlier herein.

The synthesis of a hemagglutinin molecule by VFP-11 infected cells was confirmed by immune precipitation from metabolically radiolabeled infected cell lysates using specific anti H5-antibody and standard techniques. The specific immune precipitation of precursor hemagglutinin with a molecular weight of approximately 63 kd (kilodaltons) and two cleavage products with molecular weights of 44 and 23 kd was demonstrated. No such proteins were precipitated from a lysate of uninfected CEF cells or parental virus, FP-1, infected cells.

To determine that the HA molecule produced in cells infected with the recombinant fowlpox, vFP-11, was expressed on the cell surface, immunofluorescence studies were performed. CEF cells infected with the recombinant fowlpox virus, vFP-11, showed strong surface fluorescent staining. In cells infected with the parental virus, FP-1, no fluorescence was detected.

Plasmid pRW 759 was created as follows:

pRW 742B (cf. Example 4) is linearized by partial digestion with Pst I and the fragment is recut with EcoRV to remove the rabies G gene, leaving the HH promoter on the remaining fragment of about 3.4 Kbp. This is treated with alkaline phosphatase and a synthetic oligonucleotide was inserted for joining of the HH promoter with TYHA at ATG to generate pRW 744.

This plasmid was linearized by partial digestion with Dra I, the linear fragment was cut with Sal I, and the larger fragment was reisolated and treated with alkaline phosphatase.

Finally, pRW 759 was generated by inserting into the pRW 744 vector the isolated Sal I-Dra I coding sequence of TYHA, disclosed by Kawaoka et al., Virology 158, 218-227 (1987).

EXAMPLE 10

Immunization with vFP-11 to Protect Birds against Challenge with Live Influenza Virus In order to assess the immunogenicity of the recombinant fowlpox virus vFP-11, vaccination and challenge experiments were performed in chickens and turkeys.

Specific pathogen free white leghorn chickens were vaccinated at 2 days and 5 weeks of age by wing web puncture with a double needle used for commercial vaccination of poultry with fowlpox virus. Approximately 2 ul containing $6 \times 10^5$ pfu of vPF-11 was given to each bird. The older birds were bled before vaccination, and all birds were bled prior to challenge and two weeks later.

For comparative purposes, a second group of chickens was vaccinated with a conventional H5 vaccine consisting of an inactivated H5N2 strain in a water-in-oil emulsion.

Inactivated H5N2 vaccine was prepared from A/Mallard/NY/189/82 (H5N2) influenza virus grown in 11 day embryonated chicken eggs; the infected allantoic fluid with an HA titer of 800/0.1 ml and infectivity titer of $10^{8.5}/0.1$ ml was inactivated with 0.1% propiolactone and suspended in water-in-oil emulsion as described in Stone et al., Avian Dis. 22, 666-674 (1978) and Brugh et al., Proc. Second Inter. Sym. on Avian Influenza, 283-292 (1986). The vaccine in 0.2 ml volume was administered to 2 day and 5 week old SPF white leghorn chickens by the subcutaneous route, under the skin on the inside of the thigh muscle.

A third and fourth group of chickens received parental virus FP-1 or no vaccine, respectively.

Chickens were challenged with approximately $10^3$ $LD_{50}$ of the highly pathogenic A/Turkey/Ireland/1378/83 (H5N8) or A/Chick/Penn/1370/83 (H5N2) influenza virus by administering 0.1 ml to the nares of each bird. Two day old birds were challenged 6 weeks after vaccination and 5 week old birds were challenged at 5 weeks post vaccination. The birds were observed daily for disease signs indicated by swelling and cyanosis of the face and comb and hemorrhage of the legs (such birds could frequently not stand), paralysis and death. Most deaths occurred between 4 and 7 days after infection. Tracheal and cloacal swabs were taken of each live chicken 3 days after infection and screened for virus by inoculation into embryonated eggs. The chickens inoculated with either wildtype or recombinant fowlpox virus developed typical lesions on the wing web. Pustules formed by the third day at the site of each needle stick, cellular infiltration followed with scab formation and recovery by 7 days. There were no secondary lesions formed and there was no evidence of spread to non- vaccinated contact chickens. The results of the challenge experiment are shown in Table VIII and the associated serological findings in Table IX.

TABLE VIII

| Protection of Chickens Mediated by H5 Expressed in Fowl Pox | | | | | |
|---|---|---|---|---|---|
| Challenge | | Age of | Protection | Virus detected | |
| Virus | Vaccine | Chickens | Sick/Dead/Total | Trachea | Cloaca |
| Ty/Ireland (H5N8) | Fowl Pox-H5 (vFP-11) | 2-day | 0/0/10 | 0/10 | 0/10 |
| | | 5 weeks | 0/0/5 | 0/5 | 0/5 |
| | Inactivated H5N2 | 2-day | 0/0/9 | 0/9 | 0/9 |
| | | 5 weeks | 0/0/5 | 0/5 | 0/5 |
| | Fowl Pox control | 2-day | 10/9/10 | 2/6 | 3/6 |
| | | 5 weeks | 4/3/5 | 0/5 | 4/5 |
| | None | 2-day | 10/9/10 | 2/7 | 5/7 |
| | | 2-day* | 2/1/2 | 2/2 | 2/2 |

TABLE VIII-continued

Protection of Chickens Mediated by H5 Expressed in Fowl Pox

| Challenge Virus | Vaccine | Age of Chickens | Protection Sick/Dead/Total | Virus detected Trachea | Cloaca |
|---|---|---|---|---|---|
| Ck/Penn (H5N2) | Fowl Pox-H5 (vFP-11) | 5 weeks | 2/2/5 | 0/5 | 1/5 |
| | | 2-day | 0/0/10 | 8/10 | 0/10 |
| | | 5 weeks | 0/0/6 | 5/6 | 2/6 |
| | Inactivated H5N2 | 2-day | 0/0/8 | 2/8 | 0/8 |
| | | 5 weeks | 0/0/5 | 3/5 | 0/5 |
| | Fowl Pox control | 2-day | 10/1/10 | 10/10 | 10/10 |
| | | 5 weeks | 5/0/5 | 5/5 | 5/5 |
| | None | 2-day | 9/3/9 | 9/9 | 9/9 |
| | | 2-day* | 2/2/2 | 2/2 | 2/2 |
| | | 5 weeks | 5/2/5 | 5/5 | 5/5 |

*Four non-vaccinated birds were housed and raised with the Fowl Pox-H5 group of 10 birds to test for spread of Fowl Pox-H5.

TABLE IX

Serological Response Induced by Inoculation with vFP-11 or an Inactivated Influenza Virus Vaccine

| | | | HI titers to:[a] | | | | Neutralization of Infectivity | | | |
|---|---|---|---|---|---|---|---|---|---|---|
| Challenge | | Age of | Ty/Ireland | | Ck/Penn | | Ty/Ireland | | Ck/Penn | |
| Virus | Vaccine | Chickens | Post-1 | Post-2 | Post-1 | Post-2 | Post-1 | Post-2 | Post-1 | Post-2 |
| Ty/Ireland (H5N8) | Fowl Pox-H5 | 2-day | 15[c] | 156 | < | 65 | 70 | 2,500 | | |
| | | 5 weeks | 100 | 480 | < | 20 | 160 | 10,000 | | |
| | Inactivated H5N2 | 2-day | 30 | 70 | 30 | 50 | 65 | 1,000 | | |
| | | 5 weeks | 350 | 600 | 180 | 200 | 240 | 2,500 | | |
| | Fowl Pox control | 2-day | < | 160[1](b) | < | 20 | < | 300[1] | | |
| | | 5 weeks | < | 1280[2] | < | 60 | < | 10,000[2] | | |
| | None | 2-day | < | 80[1] | < | 20 | < | 300[1] | | |
| | | 5 weeks | < | 2000[3] | < | 60 | < | 70[3] | | |
| Ck/Penn/ (H5N2) | Fowl Pox-H5 | 2-day | 15 | 600 | < | 90 | | | < | 70 |
| | | 5 weeks | 80 | 2500 | < | 300 | | | < | 2,500 |
| | Inactivated H5N2 | 2-day | 60 | 300 | 20 | 70 | | | 10 | 400 |
| | | 5 weeks | 300 | 500 | 100 | 200 | | | 150 | 1,500 |
| | Fowl Pox control | 2-day | < | 60[6] | < | 120 | | | < | 40 |
| | | 5 weeks | < | 90 | < | 140 | | | < | 40 |
| | None | 2-day | < | 60[6] | < | 160 | | | < | 25 |
| | | 5 weeks | < | 160[3] | < | 150 | | | < | 70 |

[a]The 5 week old birds were bled before vaccination and tested in HI and neutralization tests, none contained detectable antibody levels and the results are not shown. The 2-day old chickens were bled at 6 weeks post-vaccination (Post-1) and the 5 week old birds were bled at 5 weeks post-vaccination (Post-1); both groups were bled 2 weeks after challenge (Post-2). The FIGS. are the mean antibody titers from the same groups of chickens described in Table 1.
[b]The numbers in parenthesis are those that survived challenge.
< = less than 10
[c]Hemagglutination inhibition (HI) tests were done in microtiter plates using receptor-destroying-enzyme-treated sera. 4 HA units of Ty/Ire virus, and 0.5% chicken erythrocytes as described in Palmer et al., Immun. Series No. 6, 51-52, U.S. Dept. Health, Education and Welfare (1975). Neutralization of infectivity assays were done by incubating $10^3$ EID$_{50}$ of Ty/Ire virus with dilutions of sera for 30 minutes at room temperature, followed by inoculation of
aliquots into embryonated eggs. Virus growth was determined by hemagglutination assays after incubation of eggs for 2 days at 33° C.

Chickens inoculated with the fowlpox-H5 recombinant (vFP-11) or the inactivated H5N2 influenza vaccine in adjuvant were protected from challenge with the homologous Ty/Ire (H5N8) influenza virus and with the related but distinguishable Ck/Penn (H5N2) influenza virus. In contrast the majority of birds inoculated with parental FPV or that received no vaccines had clinical signs of highly pathogenic influenza including swelling and cyanosis of the face and comb, hemorrhage of the legs and paralysis. The majority of these birds died. The vaccinated birds did not shed detectable levels of Ty/Ire but did shed Ck/Penn.

Both the inactivated and recombinant vaccines induced HI and neutralizing antibodies to Ty/Ire but the levels of antibody induced by the fowlpox-H5 recombinant, vFP-11, prior to challenge did not inhibit HA or neutralize the heterologous Ck/Penn H5. Regardless, the chickens were protected from challenge with both Ty/Ire and Ck/Penn influenza viruses.

Immunity to H5 influenza induced by the vFP-11 vaccination lasted for at least 4 to 6 weeks and was crossreactive. To investigate further the duration and specificity of the response, a group of 4 week old chickens was inoculated in the wing web with vFP-11 as described previously and challenged at monthly intervals with the cross reactive Ck/Penn virus. Again, no HI antibodies were detectable prior to challenge. Nonetheless, birds were protected beyond four months.

The H5 expressed by vFP-11 also induces a protective immune response in turkeys. Outbread white turkeys were vaccinated at 2 days and 4 weeks of age by wing-web inoculation as previously described. The results are shown in Table X.

TABLE X

Protection of Turkeys Mediated by H5-HA Expressed in vFP-11

| Vaccine | Age of birds | Protection sick/dead/total | Virus Detection trachea | cloaca | HI antibody Ty/Ire Post 1 | Post-2 | Neutralizing antibody $\log_{(10)}$ to Ty/Ire Post-1 | Post-2 |
|---|---|---|---|---|---|---|---|---|
| vFP-11 | 2-day | 1/1/5 | 5/5 | 3/5 | <10 | 160 | <1 | 4.32 |

TABLE X-continued

Protection of Turkeys Mediated by H5-HA Expressed in vFP-11

| Vaccine | Age of birds | Protection sick/dead/total | Virus Detection trachea | Virus Detection cloaca | H1 antibody Ty/Ire Post-1 | H1 antibody Ty/Ire Post-2 | Neutralizing antibody $\log_{(10)}$ to Ty/Ire Post-1 | Neutralizing antibody $\log_{(10)}$ to Ty/Ire Post-2 |
|---|---|---|---|---|---|---|---|---|
| recombinant | 4-week | 2/1/6 | 2/6 | 0/6 | <10 | 640 | 1.05 | 4.16 |
| Contact | 2-day | 2/2/2 | 2/2 | 2/2 | <10 | dead | <1 | dead |
| controls | 4-week | 2/2/2 | 2/2 | 2/2 | <10 | dead | <1 | dead |

Significant survival against challenge with the homologous Ty/Ire virus was observed with both age groups. Non-vaccinated contact control birds were housed with the vaccinated birds to test for spread of the recombinant virus. These birds did not survive challenge.

EXAMPLE 11

Construction of Fowlpox Virus FP-1 Recombinant vFP 12 Expressing Chicken Influenza Nucleoprotein (NP) Gene Plasmid pNP 33 contains a cDNA clone of the influenza virus Chicken/Pennsylvania/1/83 nucleoprotein gene (NP). Only the 5' and 3' ends of the approximately 1.6 Kbp NP gene have been sequenced. NP was moved from pNP 33 into Sma I digested pUC 9 as a blunt ended 5' Cla I-Xho I 3' fragment, with the pUC 9 Eco RI site at the 3' end, generating pRW 714. The translational initiation codon (ATG) of NP contains the following underlined Aha II site: ATGGCGTC. The vaccinia H6 promoter, previously described, was joined to the NP with a double stranded synthetic oligonucleotide. The synthetic oligonucleotide contained the H6 sequence from the Eco RV site to its ATG and into the NP coding sequence at the Aha II site. The oligonucleotide was synthesized with Bam HI and Eco RI compatible ends for insertion into pUC 9 generating pRW 755. Starting at the Bam HI compatible end, with the ATG underlined, the sequence of the double stranded synthetic oligonucleotide is:

```
GATCCGATATCCGTTAAGTTTGTATCGTAATGGCGTCG
     GCTATAGGCAATTCAAACATAGCATTACCGCAGCTTAA
```

The Aha II linear partial digestion product of pRW 755 was isolated and recut with Eco RI. The pRW 755 fragment containing a single Aha II cut at the ATG and recut with Eco RI was isolated, treated with phosphatase, and used as a vector for the pRW 714 digestion product below.

The isolated Aha II linear partial digestion product of pRW 714 was recut with Eco RI. An approximately 1.6 Kbp Aha II-Eco RI isolated fragment, containing the NP coding sequence, was inserted into the above pRW 755 vector generating pRW 757. The complete H6 promoter was formed by adding the sequences upstream (5') of the Eco RV site. The plasmid pRW 742B (described in Example 4) had the H6 sequence downstream (3') of the Eco RV site removed along with sequences through to pUC 9's Nde I site. The pRW 742B Eco RV-Nde I fragment, treated with phosphatase, was used as a vector for the pRW 757 fragment below. The isolated linear partial Eco RV digestion product of pRW 757 was re-isolated after Nde I digestion; this fragment contains the H6 promoter from the Eco RV site through NP to the pUC 9 Nde I site. The pRW 757 fragment was inserted into the pRW 742B vector to form pRW 758. The Eco RI fragment from pRW 758, containing the entire H6 promoted NP, was blunt ended with the Klenow fragment of DNA polymerase I and inserted into the pRW 731.13 Hinc II site generating pRW 760. The pRW 731.13 Hinc II site is the FP-1 locus used in Example 6 for construction of vFP-6 and vFP-7.

Using fowlpox FP-1 as the rescuing virus, plasmid pRW 760 was used in an invitro recombination test. Progeny plaques were assayed and plaque purified using in situ plaque hybridization. Expression of the gene has been confirmed by immune precipitation studies using a goat polyclonal anti-NP antiserum. The size of the protein specifically precipitated from a lysate of vFP-12 infected CEF cells was approximately 55 KD, within the published range of influenza virus nucleoproteins.

EXAMPLE 12

Production of a Fowlpox Virus Double Recombinant vFP-15 Expressing the Avian Influenza Nucleoprotein (NP) and Hemagglutinin (HA) Genes The hemagglutinin (HA) gene from A/Tyr-/Ire/1378/83 was previously described in the construction of vFP-11 (example 9). In making a double recombinant the HA gene was first moved to locus f8 previously defined in the construction of vFP-8 using plasmid pRW 731.15.

The plasmid used in the construction of vFP-11 was pRW 759. The hemagglutinin gene linked to the H6 promoter was removed from this plasmid by a Pst I partial digest. This fragment was then blunt-ended with the Klenow fragment of DNA polymerase I and inserted into the blunt-ended Bam HI site of pRW 731.15 to create pRW 771.

Plasmid pRW 771 was then used in an in vitro recombination test using vFP-12 as the rescuing virus. The vFP-12 recombinant virus contains the nucleoprotein gene linked to the H6 promoter at locus f7 defined in plasmid pRW 731.13. Recombinant plaques now containing both insertions were selected and plaque purified by in situ hybridization and surface expression of the hemagglutinin confirmed by a Protein-A-Beta-galactosidase linked immunoassay. Expression of both genes was confirmed by immune precipitation from the double recombinant virus, vFP-15, infected cell lysates.

EXAMPLE 13

Construction of Recombinant Canarypox Viruses

The following example demonstrates identification of four non-essential insertion loci in the canarypox genome and the construction of four recombinant canarypox viruses vCP-16, vCP-17, vCP-19 and vCP-20.

The recombinant canarypox vCP-16 was constructed as follows.

A 3.4 Kbp Pvu II canarypox DNA fragment was cloned into pUC 9 to produce pRW 764.2. A unique Eco RI site was found asymmetrically located within the fragment with a short arm of 700 bp and a long arm of 2.7 Kbp. The plasmid was digested with Eco RI and blunt-ended using the Klenow fragment of DNA polymerase I. The blunt-ended H6/rabies G gene was then ligated into this site and used to transform E. coli. The resulting plasmid pRW 775 was used in an in vitro recombination test. Progeny plaques positive on an immunoscreen were selected and plaque purified. The resulting recombinant was designated vCP-16 and the insertion locus as C3.

The plasmid pRW 764.2 used in the construction above also contained a unique Bgl II site approximately 2.4 Kbp from the Eco RI site. Using the same cloning strategy the H6/rabies G gene was ligated into plasmid pRW 764.2 at this site to produce pRW 774. This plasmid was used in the construction of recombinant vCP-17 with the insertion locus designated as C4.

Plasmid pRW 764.5 contains an 850 bp Pvu II fragment of canarypox DNA with a unique Bgl II site assymmetric within the fragment 400 bp from one terminus. Using the same cloning strategy previously described the rabies G gene linked to the H6 promoter was inserted at this site to produce pRW 777. The stable recombinant virus produced was designated vCP-19 and the insertion locus C5.

Plasmid pRW 764.7 contains a 1.2 Kbp Pvu II fragment with a unique Bgl II site 300 bases from one terminus. The plasmid was digested with Bgl II and blunt-ended with the Klenow fragment of DNA polymerase I. The blunt-ended 11K promoted Lac Z gene was inserted to produce plasmid pRW 778. The stable recombinant virus produced using this plasmid was designated vCP-20 and the insertion locus designated C6.

EXAMPLE 14

Construction of Fowlpox Virus Recombinant vFP-29 Expressing the Fusion Protein of Newcastle Disease Virus Plasmid pNDV 108, the cDNA clone of the fusion gene of NDV Texas Strain, consisted of an Hpa I cDNA fragment of approximately 3.3 Kbp containing the fusion protein coding sequence as well as additional NDV coding sequences cloned into the Sca I site of pBR 322. Steps in the production of the insertion plasmid are described below.

(1) Creation of plasmid pCE 11

An FPV insertion vector, pCE 11, was constructed by inserting polylinkers at the Hinc II site of pRW 731.13 (designated as locus f7). pRW 731.13 contains a 5.5 Kbp Pvu II fragment of FP-1 DNA. A nonessential locus was previously defined at the Hinc II site by the construction of the stable recombinant vFP-6 previously described in Example 6. The polylinkers inserted at the Hinc II site contain the following restriction enzyme sites: Nru I, Eco RI, Sac I, Kpn I, Sma I, Bam HI, Xba I, Hinc II, Sal I, Acc I, Pst I, Sph I, Hind III and Hpa I.

(2) Creation of plasmid pCE 19

This plasmid is a further modification of pCE 11, in which the vaccinia virus transcriptional stop signal ATTTTTNT (L. Yuen and B. Moss, J. Virology 60, 320–323 [1986]) (where N in this case is an A) has been inserted between the Sac I and Eco RI sites of pCE 11 with the consequent loss of the Eco RI site.

(3) Insertion of NDV coding sequences

A 1.8 Kbp gel-purified Bam HI fragment containing all but 22 nucleotides from the 5' end of the fusion protein gene was inserted into the Bam HI site of pUC 18 to form pCE 13. This plasmid was digested with Sal I which cuts in the vector 12 bases upstream of the 5' end of the coding sequence. The ends were filled in with the Klenow fragment of DNA Polymerase I and the plasmid further digested with Hind III which cuts 18 bases upstream of the Sal I site. A gel purified 146 bp Sma I-Hind III fragment containing the vaccinia virus H6 promoter previously described in preferred embodiments as well as polylinker sequences at each termini was ligated to the vector and transformed into E. coli cells. The resulting plasmid was designated pCE 16.

In order to align the initiating ATG codon of the NDV fusion protein gene with the 3' end of the H6 promoter and to replace the 22 nucleotides missing from the NDV 5' end in pCE 16, complementary synthetic oligonucleotides were designed ending in Eco RV and Kpn I sites. The oligonucleotide sequence was 5' ATC-CGT-TAA-GTT-TGT-ATC-GTA-ATG-GGC-TCC-AGA-TCT-TCT-ACC-AGG-ATC-CCG-GTA-C 3'.

The construct pCE 16 was then digested with Eco RV and Kpn I. The Eco RV site occurs in the H6 promoter 24 bases upstream of the initiating ATG. The Kpn I site occurs in the NDV coding sequence 29 bases downstream of the ATG.

Oligonucleotides were annealed, phosphorylated and ligated to the linearized plasmid and the resulting DNA used to transform E. coli cells. This plasmid was designated pCE 18.

In order to insert the NDV coding sequence into an FPV insertion vector, a gel purified 1.9 Kbp Sma I-Hind III fragment of pCE 18 (cutting in the polylinker region) was ligated to a 7.8 Kbp Sma I-Hind III fragment of pCE 19 described above. The transcriptional stop signal occurs 16 bases downstream of the Sma I site. The resulting plasmid was designated pCE 20.

The plasmid pCE 20 was used in an in vitro recombination test using fowlpox virus FP-1 as the rescuing virus. The resulting progeny were plated on CEF monolayers and the plaques subjected to a Beta-galactosidase linked Protein-A immunoscreen using a polyclonal anti-NDV chicken serum. Positively staining plaques were selected and subjected to four rounds of plaque purification to achieve a homogeneous population. The recombinant was designated vFP-29.

EXAMPLE 15

Construction of Avipox Virus Recombinants Expressing the Feline Leukemia Virus (FeLV) Envelope (ENV) Glycoprotein The FeLV env gene contains the sequences which encode the p70+p15E polyprotein. This gene was initially inserted into the plasmid pSD467vC with the vaccinia H6 promoter juxtaposed 5' to the FeLV env gene. The plasmid pSD467vC was derived by first inserting an 1802 bp Sal I/Hind III fragment containing the vaccinia hemagglutinin (HA) gene into a pUC18 vector. The location of the HA gene was defined previously (Shida, Virology 150, 451–462, [1988]). The majority of the open reading frame encoding the HA gene product was deleted (nucleotide 443 through nucleotide 1311) and a multiple cloning site was inserted containing the Bgl II, Sma I, Pst I, and Eag I restriction endonuclease sites. The resultant pSD467vC plasmid contains vaccinia flanking arms of 442 bp upstream of the multiple cloning site and 491 bp downstream from these restriction sites. These flanking arms enable genetic material inserted into the multiple cloning region to be recombined into the HA region of the Copenhagen strain of vaccinia virus. The resultant recombinant progeny are HA negative.

The H6 promoter was synthesized by annealing four overlapping oligonucleotides which together comprised the complete sequence described above in preferred embodiments. The resultant 132 bp fragment contained a Bgl II restriction site at the 5' end and a Sma I site at the 3' end. This was inserted into pSD467vC via the Bgl II and Sma I restriction site. The resultant plasmid was designated pPT15. The FeLV env gene was inserted into the unique Pst I site of pPT15 which is just downstream of the H6 promoter. The resultant plasmid was designated pFeLV1A.

For construction of the FP-1 recombinant, the 2.4 Kbp H6/FeLV env sequences were excised from pFeLV1A by digestion with Bgl II and partial digestion with Pst I. The Bgl II site is at the 5' border of the H6 promoter sequence. The Pst I site is located 420 bp downstream from the translation termination signal for the envelope glycoprotein open reading frame.

The 2.4 Kbp H6/FeLV env sequence was inserted into pCE 11 digested with Bam HI and Pst I. The FP-1 insertion vector, pCE 11, was derived from pRW 731.13 by insertion of a multiple cloning site into the nonessential Hinc II site. This insertion vector allows for the generation of FP-1 recombinants harboring foreign genes in locus f7 of the FP-1 genome. The recombinant FP-1/FeLV insertion plasmid was then designated pFeLVF1. This construction does not provide a perfect ATG for ATG substitution.

To achieve the perfect ATG:ATG construction, a Nru I/Sst II fragment of approximately 1.4 Kbp was derived from the vaccinia virus insertion vector, pFeLV1C. The Nru I site occurs within the H6 promoter at a position 24 bp upstream from the ATG. The Sst II site is located 1.4 Kbp downstream from the ATG and 1 Kbp upstream from the translation termination signal. This Nru I/Sst II fragment was ligated to a 9.9 Kbp fragment which was generated by digestion with Sst II and by partial digestion with Nru I. This 9.9 Kbp fragment contains the 5.5 Kbp of FP-1 flanking arms, the pUC vector sequences, 1.4 Kbp of FeLV sequence corresponding to the downstream portions of the env gene, and the 5'-most sequence (approx. 100 bp) of the H6 promoter. The resultant plasmid was designated pFeLVF2. The ATG for ATG construction was confirmed by nucleotide sequence analysis.

A further FP-1 insertion vector, pFeLVF3, was derived from pFeLVF2 by removing the FeLV env sequences corresponding to the putative immunosuppressive region (Cianciolo et al., Science 230, 453–455 [1985]) (nucleotide 1548 to 1628 of coding sequence). This was accomplished by isolating a Sst II/Pst I fragment (sites described above) of approximately 1 Kbp from the vaccinia virus insertion vector pFeLV1D. The plasmid pFeLV1D is similar to pFeLV1C except that the env sequences corresponding to the immunosupressive region (nucleotide 1548 to 1628) were deleted by oligonucleotide-directed mutagenesis (Mandecki, Proc. Natl. Acad. Sci. USA 83, 7177–7181 [1987]). The 1 Kbp Sst II/Pst I fragment lacking nucleotides 1548 to 1628 was inserted into a 10.4 Kbp Sst II/Pst I fragment containing the remaining H6:FeLV env gene derived from pFeLVF2.

The insertion plasmids, pFeLVF2 and pFeLVF3, were used in in vitro recombination tests with FP-1 as the rescuing virus. Progeny of the recombination were plated on CEF monolayers and recombinant virus selected by plaque hybridization on CEF monolayers. Recombinant progeny identified by hybridization analyses were selected and subjected to 4 rounds of plaque purification to achieve a homogeneous population. An FP-1 recombinant harboring the entire FeLV env gene has been designated vFP-25 and an FP-1 recombinant containing the entire gene lacking the immunosuppressive region was designated vFP-32. Both recombinants have been shown to express the appropriate gene product by immunoprecipitation using a bovine anti-FeLV polyclonal serum (Antibodies, Inc., Davis, Calif.). Significantly, these FP-1 recombinants express the foreign FeLV env gene in the CRFK cell line (ATCC #CCL94), which is of feline origin.

For construction of the canarypox (CP) recombinants, a 2.2 Kbp fragment containing the H6:FeLV env sequences was excised from pFeLVF2 by digestion with Sma I and Hpa I. The Sma I site is at the 5' border of the H6 promoter sequence. The Hpa I site is located 180 bp downstream from the translation termination signal for the envelope glycoprotein open reading frame.

The 2.2 Kbp H6/FeLV env sequence was inserted in the non-essential Eco RI site of the insertion plasmid pRW764.2 following blunt-ending of the Eco RI site. This insertion vector allows for the generation of CP recombinants harboring foreign genes in locus C4 of the CP genome. The recombinant CP insertion plasmid was then designated pFeLVCP2. This construction provides a perfect ATG for ATG substitution.

The insertion plasmid, pFeLVCP2, was used in an in vitro recombination test with CP as the rescuing virus. Progeny of the recombinant were plated on CEF monolayers and recombinant virus selected by means of a Betagalactosidase linked Protein-A immunoscreen using a bovine anti-FeLV commercial polyclonal serum (Antibodies, Inc., Davis, Calif.). Positive staining plaques were selected and subjected to four rounds of plaque purification to achieve a homogeneous population. A recombinant expressing the entire FeLV env gene has been designated vCP-36.

EXAMPLE 16

Construction of Fowlpox Virus Recombinant vFP-22 Expressing the Rous Associated Virus Type 1 (RAV-1) Envelope (ENV) Gene The clone penvRV1PT of the RAV-1 envelope gene contains 1.1 Kbp of RAV-1 env DNA coding sequence cloned as a Kpn I-Sac I fragment into M13mp18. This fragment is intact at the 5' end but lacks part of the 3' sequence and was used in the following manipulations. A gel purified 1.1 Kbp Eco RI-Pst I fragment from penvRVIPT was inserted into the Eco RI and Pst I sites of pUC 9 to form pRW 756. This plasmid was then digested with Kpn I and Hind III cutting in the vector 59 bases upstream of the ATG. A 146 base pair Kpn I-Hind III fragment containing the previously described vaccinia H6 promoter was inserted to construct plasmid pCE 6.

In order to ensure that the initiating ATG of the RAV env gene was adjacent to the 3' end of the H6 promoter with extraneous sequences deleted, two complementary synthetic oligonucleotides were constructed with Eco RV and Ban II sites at the termini. The oligonucleotide sequence was 5' ATC-CGT-TAA-GTT-TGT-ATC-GTA-ATG-AGG-CGA-GCC-3'.

The plasmid pCE 6 was digested with Eco RV which cuts in the H6 promoter 24 bases upstream of the ATG and Ban II which cuts in the RAV env coding sequence 7 bases downstream of the ATG. The DNA segments were ligated and used to transform E. coli cells. The resulting plasmid, pCE 7, supplied to H6 promoter and correct 5' sequence for the final construction.

Clone mp19env (190), was found by restriction mapping to contain the entire RAV-1 env gene. A 1.9 Kbp Kpn I-Sac I fragment of the mp19env (190) containing the entire gene was inserted at the Kpn I and Sac I sites of pUC 18 to form pCE 3. This plasmid was digested with Hpa I which cuts 132 bases downstream of the initiating ATG in the RAV-1 coding sequence and Sac I which cuts at the 3' terminus of the gene. The FPV insertion vector pCE 11 previously described was digested with Sma I and Sac I cutting the plasmid in the polylinker region. The Hpa I-Sac I fragment of pCE 3 was ligated with pCE 11 to form pCE 14.

The plasmid pCE 7 was then digested with Xho I and Hind III to provide a 332 base pair fragment containing the H6 promoter and correct 5' sequence. Plasmid pCE 14 was digested with Hind III cutting in the polylinker region of the vector and Xho I cutting in the coding sequence. This DNA was ligated with the Hind III-Xho I fragment obtained from pCE 7 to form pCE 15, the final RAV-1 envelope gene construct.

This plasmid was used in an in vitro recombination test with fowlpox FP-1 as the rescuing virus. Progeny of the recombination was plated on CEF monolayers and plaques screened by a Beta-galactosidase linked Protein A immunoassay using an anti-RAV-1 polyclonal serum. Positively staining plaques were selected and subjected to four rounds of plaque purification to produce a homogeneous population. The recombinant produced was designated vFP-22. Immunoprecipitation experiments using vFP-22 infected CEF lysates have demonstrated the specific precipitation of two proteins with apparent molecular weights of 76.5 Kd and 30 Kd corresponding to the two gene products of the envelope gene. No precursor gene product was apparent.

In preliminary tests an immune response has been induced to the RAV-I envelope gene product in chickens inoculated with vFP-22.

EXAMPLE 17

Construction of Avipox Virus Recombinants Expressing the GP51,30 Envelope (ENV) Gene of Bovine Leukemia Virus (BLV)

(1) Construction of pBLVF 1 and pBLVF 2

The plasmids, pBLVF 1 and pBLVF 2, contain the gp51,30 env gene of BLV. In both plasmids, the BLV env gene is under the transcriptional control of the vaccinia virus H6 promoter and is cloned between fowlpox flanking arms (locus f7). The nucleotide sequence of the two plasmids is identical, except at codon positions 268 and 269. (pBLVF 1 encodes a protein containing the amino acids Arg-Ser at these two positions, whereas pBLVF 2 encodes a protein containing the amino acids Gln-Thr).

pBLVF 1 and pBLVF 2 were constructed by the following procedure. Plasmid pNS97-1, a plasmid containing the entire BLV env gene, was cut with Bam H1 and partially cut with Mst II. The 2.3 Kbp fragment containing the entire gp51,30 gene was isolated on an agarose gel and the sticky ends filled in with *E. coli* DNA polymerase I (Klenow fragment). Pst I linkers were then ligated onto the ends of the fragment, which after Pst I digestion, was ligated into the Pst I site of pTP 15 (Example 15). This places the BLV gene next to the vaccinia H6 promoter. (pTP15 contains the vaccinia H6 promoter cloned at a nonessential locus in the vaccinia genome.

This plasmid was then cut with Eco RV and partially cut with Ava II. The 5.2 Kbp fragment was isolated and the oligonucleotides 5'-ATCCGTTAAGTTTGTATCGTAATGCCCAAAGAACGACG-3' and 5'GACCGTCGTTCTTTGGGCATTACGATACAAACTTAACGGAT-3' used to recircularize the plasmid. This removes unnecessary bases between the BLV gene and the H6 promoter.

The resulting plasmid was cut with Pst I and partially cut with Bgl II and the 1.7 Kbp fragment containing the H6 promoted-BLV gene cloned into the Bam HI-Pst I site of pCE 11, the fowlpox virus insertion vector previously described using locus f7. This places the H6 promoted-BLV gene between fowlpox flanking arms. This plasmid was designated pBLVF 1.

An identical procedure was used to construct pBLVF 2, with the exception that an additional in vitro mutagenesis step was performed before cloning the H6 promoted-BLV gene into pCE 11. This mutagenesis was performed by the following procedure. Plasmid pNS97-1 was cut with Xma I and partially cut with Stu I. The 5.2 Kbp fragment was isolated and the oligonucleotides 5'-CCGGGTCAGACAAACTCCCGTCGCAGCCCTGACCTTAGG-3' and 5'-CCTAAGGTCAGGGCTGCGACGGGAGTTTGTCTGAC-3' used to recircularize the plasmid. This changes the nucleotide sequence of codons 268 and 269 from CGC-AGT to CAA-ACT.

(2) Construction of Recombinant Viruses

The plasmids pBLVF 1 and pBLVF 2 were used in an in vitro recombination test using FP-1 as the rescuing virus. Recombinant progeny was selected by in situ plaque hybridization and when the population was judged as pure by this criteria plaques were screened in an Beta-galactosidase-Protein A immunoassay using a BLV gp specific monoclonal antibody preparation. Both recombinants vFP 23 and vFP 24 produced from plasmid pBLVF 1 and pBLVF 2 respectively showed positive staining in the immunoscreen indicating that an immunologically recognizable glycoprotein was expressed on the infected cell surface.

The plasmids, pBLVK 4 and pBLVK 6 contain the BLV env gp51,30 gene and the BLV gp51,30 cleavage minus gene, respectively. Both genes are cloned into the unique Eco RI site of pRW 764.2 (locus C3) (pRW 764.2 is described in Example 13) and are under the transcriptional control of vaccinia H6 promoter.

The plasmids were derived by the following procedure: pBLVF 1 and pBLVF 2 were cut with the restriction enzyme Hind III. The oligonucleotide BKL 1 (AGCTTGAATTCA) was cloned into this site, thereby generating an Eco RI site 3' to the BLV gene.

Since there is also an Eco RI site 5' to the BLV gene, these plasmids (pBLVK 1 and pBLVK 2) were cut with Eco RI and the fragment containing the H6 promoted-BLV gene was cloned into the Eco RI site of pRW 764.2. The resulting plasmids were designated pBLVK 4 and pBLVK 6, respectively. These plasmids were used in an in vitro recombination test with canarypox as the rescuing virus. Recombinants were selected and purified on the basis of surface expression of the glycoprotein as detected in an immunoassay. The recombinants were designated vCP 27 and vCP 28 from plasmids pBLVK 4 and pBLVK 6, respectively.

Fowlpox recombinants vFP23 and vFP24 have been inoculated into sheep and bovines by a variety of routes. Animals were given two inoculations, the second at 45 days after the first. Serum samples were taken 5 weeks after the first inoculation and two weeks after the second inoculation. Antibody to gp51 was measured in a competitive ELISA test and the titer expressed as the reciprocal of the serum dilution giving a 50% reduction of competition. The results are shown in Table XI.

None of the species tested showed a detectable immune response after the primary inoculation. Both sheep and bovines showed a significant antibody rise after the secondary inoculation.

TABLE XI

Inoculation of Sheep and Bovines with vFP23 and vFP24

| Animal | Virus | Dose and Route 1° | 2° | ELISA Titer 1° | 2° |
|---|---|---|---|---|---|
| Bovine B56 | FP-1 | $10^8 + 10^{8a}$ | $10^8 + 10^8$ | 0 | 0 |
| B59 | FP-1 | ID | subcut. | 0 | 0 |
| Sheep M89 | FP-1 | | | 0 | 0 |
| M91 | FP-1 | | | 0 | 0 |
| Bovine B62 | vFP-23 | $10^8 + 10^8$ | $10^8 + 10^8$ | 0 | $200^b$ |
| B63 | vFP-23 | ID | subcut. | 0 | 80 |
| Sheep M83 | vFP-23 | | | 0 | 80 |
| M84 | vFP-23 | | | 0 | 500 |
| M85 | vFP-23 | | | 0 | 100 |
| Bovine B52 | vFP-24 | $10^8 + 10^8$ | $10^8 + 10^8$ | 0 | 200 |
| B53 | vFP-24 | ID | subcut. | 0 | 60 |
| Sheep M87 | vFP-24 | | | 0 | 200 |
| M92 | vFP-24 | | | 0 | 20 |
| M93 | vFP-24 | | | 0 | 20 |

[a]Intradermal injections were at two points
[b]Titer expressed as the reciprocal of the dilution giving 50% competition

EXAMPLE 18

Construction of Fowlpox Virus FP-1 Recombinant vFP-26 Expressing the Infectious Bronchitis Virus Mass 41 Matrix Gene Plasmid pIBVM63 contains an infectious bronchitis virus (IBV) cDNA clone of the Mass 41 strain matrix gene. An 8 Kbp Eco RI fragment of pIBVM63 contains the matrix gene with the peplomer gene upstream (5') and further upstream there is an Eco RV site. Plasmid pRW 715 has an Eco RI linker joining the two Pvu II sites of pUC 9. The 8 Kbp Eco RI fragment from pIBVM63 was inserted into the pRW 715 Eco RI site generating pRW763. Plasmid pRW 776 was created to delete the 5' Eco RI site in pRW 763, leaving a unique Eco RI site downstream (3') of the matrix gene. The isolated linear Eco RI partial digestion product of pRW 763 was recut with Eco RV. The largest fragment was isolated, blunt ended with the Klenow fragment of DNA polymerase I and self ligated generating pRW 776. The construct pRW 776 has the complete IBV peplomer and matrix genes followed by a single Eco RI site.

Only the 5' and 3' ends of the approximately 0.9 Kbp matrix gene have been sequenced. The 5' sequence of the matrix gene, starting at the translational initiation codon (ATG), contains the following underlined Rsa I site: ATGTCCAACGAGACAAATTGTAC. The previously describe H6 promoter was joined to the matrix gene with a synthetic oligonucleotide. The synthetic oligonucleotide contained the H6 sequence from its Eco RV site to the ATG and into the matrix coding sequence through the first Rsa I site. The oligonucleotide was synthesized with Bam HI and Eco RI compatible ends for insertion into pUC 9 generating pRW 772. The Eco RI end is 3' to the Rsa I site. Starting at the Bam HI compatible end, with the ATG underlined, the sequence of the double stranded synthetic oligonucleotide is:

GATCGCGATATCCGTTAAGTTTGTATCGTA<u>ATG</u>TCCAACGAGACAAATTGTACG
CGCTATAGGCAATTCAAACATAGCATTACAGGTTGCTCTGTTTAACATGCTTAA

The Rsa I linear partial digestion product of pRW 772 was isolated and recut with Eco RI. The pRW 772 fragment containing a single cut at the above Rsa I site and recut with Eco RI was isolated, treated with phosphatase, and used as a vector for the pRW 776 digestion product below.

The isolated Rsa I linear partial digestion product of pRW 776 was recut with Eco RI. Eco RI is just beyond the 3' end of the matrix gene. An approximately 0.8 Kbp Rsa I-Eco RI isolated fragment, containing the matrix coding sequence from the above Rsa I site, was inserted into the above pRW 772 vector generating pRW 783. The complete H6 promoter was formed by adding sequences 5' of the Eco RV site. The H6 promoter 5' end was Hinf I site blunt ended into the pUC 9 Sal I site creating an Eco RI site; 5' of the H6 promoter is the pUC 9 Hind III site. The Hind III-Eco RV fragment containing the 5' H6 promoter was inserted between the pRW 783 Hind III and Eco RV sites generating pRW 786. The pRW 786 Eco RI fragment, containing the complete H6 promoted matrix gene, was blunt ended with Klenow fragment of DNA polymerase I and inserted into the blunt ended Bam H1 site of pRW 731.15 (locus f8) generating pRW 789. The pRW 731.15 Bam HI site is the FP-1 locus used in Example 6 for construction of vFP-8.

Plasmid pRW 789 was used in the construction of vFP-26. Recombinant plaques were selected and processed by in situ plaque hybridization.

In preliminary tests an immune response has been induced to the IBV matrix protein in chickens inoculated with vFP-26.

EXAMPLE 19

Construction of Fowlpox Virus FP-1 Recombinant vFP-31 Expressing Infectious Bronchitis Virus (IBV) Peplomer The infectious bronchitis virus (IBV) Mass 41 cDNA clone pIBVM 63 and its subclone, pRW 776, have been described for the vFP-26 construction in Example 18. Subclone pRW 776 contains the 4 Kbp IBV peplomer gene followed by the matrix gene with a unique Eco RI site at the 3' end. Only the 5' and 3' ends of the approximately 4 Kbp IBV peplomer gene have been sequenced. A unique Xba I site separates the two genes. The 5' end of the peplomer gene, starting at the translational initiation codon (ATG), contains the following underlined Rsa I site: ATGTTGGTAACACCTCTTTTAC-TAGTGACTCTTTTGTGTGTAC. The previously described H6 promoter was joined to the peplomer gene with a synthetic oligonucleotide. The synthetic oligonucleotide contains the H6 promoter sequence from its Nru I site to ATG and into the peplomer coding sequence through its first Rsa I site. The oligonucleotide was synthesized with Bam HI and Eco RI compatible ends for insertion into pUC 9 generating pRW 768. The Eco RI end is 3' of the Rsa I site. Starting at the Bam HI compatible end, with the ATG underlined, the sequence of the double stranded synthetic oligonucleotide is:

```
GATCTCGCGATATCCGTTAAGTTTGTATCGTAATGTTGGTAACACCTCTT
     AGCGCTATAGGCAATTCAAACATAGCATTACAACCATTGTGGAGAA
TTACTAGTGACTCTTTTGTGTGTACG
AATGATCACTGAGAAAACACACATGCTTAA
```

Pst I site. The 5' sequence of HSV gD, starting at the translational initiation codon (ATG), contains the following underlined Nco I site: ATGGGGGGGGCTGCCG-CCAGGTTGGGGGCCGT-GATTTTGTTTGTCGTCATAGTGGGCCT-CCATGG. The previously described vaccinia H6 promoter was joined to the HSV gD gene with a synthetic oligonucleotide. The synthetic oligonucleotide contains the 3' portion of the H6 promoter from Nru I to ATG into the gD coding sequence through the Nco I site. The oligonucleotide was synthesized with a 5' Pst I compatible end. The gD clone in pUC9 was cut with Pst I and Nco I, and the 5' HSV sequence removed, for replacement with the synthetic oligonucleotide resulting in pRW 787. The sequence of the double stranded synthetic oligonucleotide is:

```
                GTCGCGATATCCGTTAAGTTTGTATCGTAATGGGAGGTGCCGCAGCTAGATTAG
     ACGTCAGCGCTATAGGCAATTCAAACATAGCATTACCCTCCACGGCGTCGATCTAATC
GTGCTGTTATTTTATTTGTAGTTATAGTAGGACTC
CACGACAATAAAATAAACATCAATATCATCCTGAGGTAC
```

The pRW 768 isolated linear partial Rsa I digestion product was recut with Eco RI. The pRW 768 fragment containing a single cut at the above Rsa I site and recut with Eco RI was isolated, treated with phosphatase, and used as a vector for the pRW 776 digestion product below.

The pRW 776 isolated linear partial Rsa I digestion product was recut with Eco RI. The 5 Kbp pRW 776 fragment containing a single cut at the above Rsa I site to the Eco RI site was isolated; the fragment contains IBV sequences from the above peplomer Rsa I site to the Eco RI site at the 3′ end of the matrix gene. Insertion of the pRW 776 fragment into the above pRW 768 vector generated pRW 788. The matrix gene was removed at the Xba I site noted above. The 5′ H6 promoter was added at the Nru I site by insertion of the 4 Kbp pRW 788 Nru I-Xba I blunt ended fragment into the pRW 760 Nru I-Bam HI blunt ended vector generating pRW 790. The vector pRW 760 is described in Example 11; briefly, it is vaccinia H6 promoted influenza nucleoprotein flanked by the nonessential FP-1 locus f7. The pRW 760 vector was made by removing the 3′ H6 sequences from the Nru I site through the end of the nucleoprotein at Bam HI. pRW 790 is H6 promoted IBV peplomer in the pRW 731.13 Hinc II site. Recombination of the donor plasmid pRW 790 with FP-1 resulted in vFP-31. Immunoprecipitation experiments using CEF lysates prepared from vFP-31 infected cells have demonstrated specific precipitation of a small amount of precursor protein with a molecular weight of approximately 180 Kd and of the clevage products of 90 Kd.

EXAMPLE 20

Construction of Fowlpox Virus FP-1 Recombinant vFP-30 Expressing Herpes Simplex Virus gD The herpes simplex virus (HSV) type 1 strain KOS glycoprotein D gene (gD) was cloned into the pUC 9 Bam HI site as a 5′ Bam HI linked Hpa II to 3′ Bam HI linked Nru I fragment; the 5′ end is next to the pUC 9 Pst I site.

Digestion of pRW 787 with Nru I and Bam H1 generates an approximately 1.3 Kbp fragment containing the 3′ H6 promoter, from the Nru I site, through the HSV gD coding sequence to the Bam HI site. The pRW 760 vector, cut with Nru I and Bam HI, has been described in Example 11. Insertion of the 1.3 Kbp fragment into the pRW 760 vector generated pRW 791. The pRW 791 vector contains the complete vaccinia H6 promoted HSV gD gene in the nonessential FP-1 Hinc II site in pRW 731.13. (locus f7).

Recombination of the donor plasmid pRW 791 with FP-1 resulted in vFP-30. Surface expression of the glycoprotein was detected in recombinant plaques using a Protein-A-Beta-galactosidase linked immunoassay and HSV-1 specific sera.

EXAMPLE 21

Use of Entomopox Promoters for Regulation of Expression of Foreign Genes in Poxvirus Vectors

(a) Background

Poxviruses of insects (entomopox) are currently classified in the subfamily Entomopoxvirinae which is further subdivided into three genera (A, B, and C) corresponding to entomopoxviruses isolated from the insect orders Coleoptera, Lepidoptera, and Orthoptera respectively. Entomopox viruses have a narrow host range in nature, and are not known to replicate in any vertebrate species.

The entomopox virus used in these studies was originally isolated from infected *Amsacta moorei* (Lepidoptera: arctildae) larvae from India. (Roberts and Granados, J. Invertebr. Pathol. 12, 141-143 [1968]). The virus, designated AmEPV, is the type species for genus B.

Wild-type AmEPV was obtained from Dr. R. Granados (Boyce Thompson Institute, Cornell University) as infectious hemolymph from infected *Estigmene acrea* larvae. The virus was found to replicate in an invertebrate cell line, IPLB-LD652Y, derived from ovarial tissues of *Lymantria dispar* (gypsy moth) (described by Goodwin et al., In Vitro 14, 485-494 [1978]). The cells were grown in IPL-528 media supplemented with 4% fetal calf and 4% chicken sera at 28° C.

The wild-type virus was plaque assayed on LD652Y cells and one plaque, designated V1, was selected for subsequent experiments. This isolate produces numerous occlusion bodies (OBs) in the cytoplasm of the infected cells late in the infectious cycle.

(b) Promoter Identification

The identification and mapping of an AmEPV promoter was accomplished as follows. Total RNA from late infected LD652Y cells (48 hr. post infection) was isolated and used to make 32P-labelled, first strand cDNA. The cDNA was then used to probe blots containing restriction digests of the AmEPV genome. This Southern blot detected a strong signal on a 2.6 kb Cla I fragment, indicating that the fragment encoded a strongly expressed gene. The fragment was cloned into a plasmid vector and its DNA sequence determined.

Analysis of the sequence data revealed an open reading frame capable of encoding a 42 Kd polypeptide. In vitro translation of the total RNA at 48 hr. post infection and separation of the products by SDS-PAGE revealed a polypeptide of approximately 42 Kd.

(c) Construction of a Recombinant Vaccinia Virus with Expression of a Foreign Gene Under the Control of the Entomopox Promoter In order to determine if an entomopox promoter would function in a vertebrate poxvirus system, the following plasmid was constructed. An oligonucleotide was chemically synthesized which contained the 107 bases 5' of the 42K gene translational start signal (hereafter referred to as the AmEPV 42K promoter) flanked by a Bgl II site at the 5' end and the first 14 bases of the hepatitis B virus pre-S2 coding region, which terminates in an Eco RI site, at the 3' end. The AmEPV 42K promoter sequence is described below.

```
TCAAAAAAATATAAATGATTCACCATC
TGATAGAAAAAAATTTATTGGGAAGA
ATATGATAATATTTTGGGATTTCAAA
ATTGAAAATATATAATTACAATATAAAATG
```

The AmEPV 42K promoter was ligated to the hepatitis B virus surface antigen (HBVsAg) as follows. A pUC plasmid was constructed containing the hepatitis B virus surface antigen and pre-S2 coding region (type ayw described by Galibert et al., Nature 281, 646-650 [1979]) flanked by vaccinia virus arms in the non-essential region of the vaccinia virus genome which encodes the hemagglutinin (HA) molecule (HA arms described in Example 15; HA region described by Shida, Virology 150, 451-462 [1986]). The oligonucleotide described above was inserted into this plasmid using the unique EcoR I site in the HBVsAg coding region and a unique Bgl II site in the HA vaccinia arm. The resulting recombinant vaccinia virus was designated vP 547.

Expression of the inserted HBVsAg coding sequence under the control of the entomopox 42K promoter was confirmed using an immunoassay. Equivalent cultures of the mammalian cell line BSC-40 were infected with parental vaccinia virus or recombinant vP 547. At 24 hours post-infection cells were lysed and the lysate applied in serial dilutions to a nitrocellulose membrane. The membrane was first incubated with a goat anti-HBV serum and then with $^{125}$I-Protein A. After washing, the membrane was exposed to X-ray film. Positive signals were detected in vP 547 infected cultures but not in parental virus infected cultures, indicating recognition of the AmEPV 42K promoter by vaccinia virus in mammalian cells.

The above results were verified using an Ausria assay (see Example 1 for details) to detect HBVsAg in infected mammalian cells. Vaccinia virus recombinants containing the HBsAg gene coupled to the AmEPV42K or vaccinia virus H6 promoter were used to infect BSC-40 cells and the level of expression of sAg assayed by the Ausria test. As presented in Table XII, the data shows that the level of expression of HBsAg using the 42K promoter was significant.

TABLE XII

| Expression of HBVsAg in Recombinant Vaccinia Virus | | |
|---|---|---|
| Recombinant Virus | Promoter | Ausria P/N Ratio |
| vP410 | Control | 1.0 |
| vP481 | H6 | 24.3 |
| vP547 | 42K | 44.9 |

Further experiments were conducted to ascertain the temporal nature of the regulation of the AmEPV 42K promoter in a vertebrate poxvirus background. Equivalent cultures of BSC-40 cells were infected with vP 547 in the presence or absence of 40 ug/ml of cytosine arabinoside, an inhibitor of DNA replication which therefore blocks late viral transcription. Levels of expression at 24 hours post-infection were assayed in an Ausria test. The results indicated that the 42K promoter was recognized as an early promoter in a vaccinia virus replication system.

Note that the use of the AmEPV 42K promoter for the expression of foreign genes in a mammalian system is clearly distinct from the use of the *Autographa californica* NPV polyhedrin promoter for gene expression in invertebrate systems (Luckow and Summers, Biotechnology 6, 47-55 [1988]). The polyhedrin promoter is not recognized by the transcriptional apparatus in mammalian cells (Tjla et al., Virology 125, 107-117 [1983]). The use of the AmEPV 42K promoter in mammalian cells represents the first time an insect virus promoter has been utilized for the expression of foreign genes in a non-insect viral vector in non-invertebrate cells.

In order to determine whether avipox viruses would also recognize the 42K entomopox promoter, the following experiment was performed. Identical cultures of CEF cells were inoculated at 10 pfu per cell with either fowlpox virus, canarypox virus or vaccinia virus, and simultaneously transfected with 25 ug of one of the following plasmids 1) plasmid 42K.17 containing the HBV pre-S$_2$+sAg coding sequence linked to the 42K promoter or 2) plasmid pMP15.spsP containing the identical HBVsAg coding sequence linked to the vaccinia virus H6 promoter previously described. After 24 hours the cultures were frozen, the cells lysed and the lysate analyzed for the presence of HBVsAg using an Ausria test (see Example 1).

The results shown in Table XIII should be viewed in a qualitative sense. They indicate that the transcriptional apparatus of both fowlpox and canarypox is able to recognize the 42K promoter and allow transcription of the linked HBVsAg coding sequence. Although levels of expression are lower than those obtained with the vaccinia virus H6 promoter, levels are well above background levels obtained with the negative controls.

TABLE XIII

Recognition of 42K Entomopox Promoter by Avipox Viruses

| Virus | Promoter | P/N Ratio |
|---|---|---|
| Fowlpox | 42K | 39.1 |
|  | H6 | 356.8 |
| Canarypox | 42K | 90.2 |
|  | H6 | 222.2 |
| Vaccinia | 42K | 369.4 |
|  | H6 | 366.9 |
| None | 42K | 7.8 |
| None | H6 | 7.2 |
| Vaccinia | — | 7.2 |

EXAMPLE 22

Immunization with VCP-16 to Protect Mice against Challenge with Live Rabies Virus Groups of 20, four to six week old mice were inoculated in the footpad with 50 to 100 ul of a range of dilutions of either of two recombinants: (a) vFP-6- the fowlpox-rabies recombinant described in Example 6, and (b) vCP-16- the canarypox-rabies recombinant described in Example 13.

At 14 days, 10 mice from each group were sacrificed and the serum collected. The anti-rabies titer in the serum was calculated using an RFFI test previously described in Example 7. The remaining 10 mice in each group were challenged by intracerebral inoculation with the CVS strain of rabies virus used in Example 7. Each mouse received 30 ul corresponding to 16 mouse LD$_{50}$. At 28 days, surviving mice were assessed and the protective dose 50 (PD$_{50}$) calculated. The results are shown in Table XIV.

The level of protection of mice found by inoculation of vFP-6 confirms the result found on inoculation of the fowlpox recombinant vFP-3 discussed in Example 7. The level of protection afforded by inoculation of vCP-16 is considerably higher. On the basis of the calculated PD$_{50}$ the canarypox-rabies recombinant is 100 times more effective in protection against rabies challenge than is the fowlpox-rabies recombinant.

TABLE XIV

Protective Immunity to Rabies Virus Challenge Elicited by Two Avipox-Rabies Recombinants

| Fowlpox vFP-6 | | | Canarypox vCP-16 | | |
|---|---|---|---|---|---|
| Inoculum Dose | RFFI Titer | Survival Ratio | Inoculum Dose | RFFI Titer | Survival Ratio |
| 7.5[a] | 2.3[b] | 7/10 | 6.5 | 2.5 | 10/10 |
| 5.5 | 1.8 | 5/10 | 4.5 | 1.9 | 6/10 |
| 3.5 | 0.7 | 0/10 | 2.5 | 1.1 | 1/10 |
| 1.5 | 0.6 | 0/10 | 0.5 | 0.4 | 0/10 |
| 1 PD$_{50}$ = 6.17 | | | 1 PD$_{50}$ = 4.18 | | |

[a]Virus titers expressed as log$_{10}$ TCID$_{50}$
[b]RFFI titer expressed as log$_{10}$ of highest serum dilution giving greater than 50% reduction in the number of fluorescing wells in an RFFI test.

EXAMPLE 23

Use of Fowlpox Promoter Elements to Express Foreign Genes

I. Identification of the Fowlpox Gene Encoding a 25.8 Kilodaltons (KD) Gene Product Visualization of protein species present in fowlpox (FP-1) infected CEF lysates by Coomassie brilliant blue staining of SDS-polyacrylamide gels revealed an abundant species with an apparent molecular weight of 25.8KD. This protein was not present in uninfected cell lysates. Pulse-experiments using $^{35}$S-methionine to radiolabel synthesized proteins at specific times post infection again demonstrated the abundance of the FP-1 induced protein and showed that it is synthesized from 6 hours to 54 hours postinfection. At its peak level this FP-1 25.8KD protein accounts for approximately 5% to 10% of total protein present in the cell lysate.

The abundance of the FP-1 induced 25.8KD protein suggested that the gene encoding this gene product is regulated by a strong FP-1 promoter element. In order to localize this promoter element for subsequent use in the expression of foreign genes in poxvirus recombinants, a polysome preparation was obtained from FP-1 infected CEF cells at 54 hours postinfection. RNA was isolated from this polysome preparation and when used to program a rabbit reticulocyte in vitro translation system generated predominantly the 25.8KD FP-1 protein.

The polysome RNA was also used as a template for first strand cDNA synthesis using oligo (dT) 12-18 as a primer. The first strand cDNA was used as a hybridization probe in Southern blot analyses with FP-1 genomic digests. Results from these hybridization analyses suggested that the gene encoding the 25.8KD protein was contained in a 10.5 Kbp Hind III fragment. This genomic Hind III fragment was subsequently isolated and ligated into a commercial vector, pBS (Stratagene, La Jolla, Calif.), and the clone was designated pFP23k-1. Further hybridization analyses using the first strand cDNA to probe digests of pFP23k-1 localized the 25.8KD gene to a 3.2 Kbp Eco RV sub-fragment. The fragment was subcloned into pBS and designated pFP23k-2.

Approximately 2.4 Kbp of this FP-1 Eco RV fragment has been sequenced by the Sanger dideoxy chain termination method (Sanger et al., Proc. Natl. Acad. Sci. USA 74, 5463-5467 [1977]). Analysis of the sequence reveals an open reading frame (ORF) which encodes a gene product with a molecular weight of 25.8KD. In vitro run-off transcription of this ORF by bacteriophage T7 polymerase (Stratagene, La Jolla, Calif.) in a pBS vector generates an RNA species which when used to program a rabbit reticulocyte in vitro translation system (Promega Biotec, Madison, Wis.) yields a polypeptide species with an apparent molecular weight of 25.8KD. This polypeptide comigrates with the abundant 25.8KD protein observed in lysates from FP-1 infected CEFs on an SDS-polyacrylamide gel. These results suggest that this is the gene encoding the abundant FP-1 induced 25.8KD gene product.

II. Use of the Upstream Promoter Elements of the FP-1 25.8KD Gene to Express Feline Leukemia Virus (FeLV) env ene in FP-1 and Vaccinia Recombinants A 270 bp Eco RV/Eco RI fragment containing the FP-1 25.8KD gene regulatory region (FP25.8K promoter) and 21 bp of the 25.8KD gene coding sequence was isolated from pFP23k-2. Below is presented the nucleotide sequence of the FP 25.8K promoter region used to derive pFeLV25.8F1 and pFeLV25.81A. This 270 nucleotide sequence provides 249 nucleotides of the region upstream of the initiation codon (ATG) for the 25.8KD gene product and the first 21 bp of the coding sequence.

```
5'—GATATCCCCATCTCTCCAGAACAGCAGCATAGTGTTAGGACAATCATCTAATGCAATA—
TCATATATGAATCTCACTCCGATAGGATACTTACCACAGCTATTATACCTTAATGTATGTT—
CTATATATTTAAAAACAGAAACAAACGGCTATAAGTTTATATGATGTCTATATTATAGTGA—
GTATATTATAAGTATGCGGGAATATCTTTGATTTAACAGCGTACGATTCGTGATAAGTAAA—
TATAGGCAATGGATAGCATAAATGAATTC—3'
```

This fragment was blunt-ended and then inserted into a Sma I digested FP-1 insertion vector (pFeLVF1; see Example 15) containing the FeLV env sequences. This insertion vector enabled recombination with the f7 locus of the FP-1 genome. Insertion of the FP25.8K promoter upstream sequences 5' to the FeLV env gene and in the proper orientation was confirmed by sequence analysis. This insertion does not provide a perfect ATG for ATG substitution but the ATG provided by the 25.8KD gene is out of frame with the FeLV env ATG, so no fusion protein is formed. The FP-1 insertion plasmid containing the FP25.8KD promoter upstream from the FeLV env gene was designated pFeLV25.8F1.

A similar construct was prepared using the vaccinia virus insertion vector, pFeLV1A, harboring the FeLV gene (see Example 15). The H6 promoter was excised from pFeLV1A by digestion with Bgl II and Sma I. Following blunt-ending of the Bgl II restriction site, the blunt ended 270 bp Eco RV/Eco RI fragment containing the FP25.8K promoter was inserted juxtaposed 5' to the FeLV env gene. This construct was confirmed by sequence analysis. There is not a perfect ATG for ATG substitution in this recombinant either but the ATG from the 25.8KD gene is not in frame with the ATG from the FeLV gene. The vaccinia (Copenhagen strain) insertion vector harboring the 25.8KD gene upstream region juxtaposed 5' to the FeLV gene was designated pFeLV25.81A.

The insertion plasmids, pFeLV25.8F1 and pFeLV25.81A, were used for in vitro recombination with FP-1 (pFeLV25.8F1) and the Copenhagen strain of vaccinia virus (pFeLV25.81A) as the rescuing viruses. Progeny of the recombination were plated on appropriate cell monolayers and recombinant virus selected by a beta-galactosidase linked Protein A Immunoscreen and a bovine anti-FeLV serum (Antibodies, Inc., Davis, Calif.). Preliminary results suggest that the FP25.8K promoter can regulate the expression of foreign genes in poxvirus recombinants.

EXAMPLE 24

Safety and Efficacy of VFP-6 and VCP-16 in Poultry

The two avipox recombinants vFP-6 and vCP-16 (described in Examples 6 and 13) were inoculated into 18 day old chicken embryos, 1 day old chickens and 28 day old chickens and the response of the birds evaluated on 3 criteria 1) effects of vaccination on hatchability, vaccinal reactions and mortality 2) the immune response induced to the rabies glycoprotein and 3) the immune response induced to fowlpox antigens. The experiments performed are described below.

A. Safety Tests

Groups of twenty 18 day old embryos were inoculated into the allantoic cavity with 3.0 or 4.0 $\log_{10}$ $TCID_{50}$ of either vFP-6 or vCP-16. After hatching the chickens were observed for 14 days when they were individually bled and the sera collected. The two recombinants inoculated in the chicken embryos had no effect on the hatchability of the eggs and the chickens remained healthy during the 14 day observation period.

Groups of 10 SPF 1 day old chickens were inoculated with 3.0 $\log_{10}$ $TCID_{50}$ of each of the recombinants by the intra-muscular route. The chickens were observed for 28 days and serum samples collected at 14 and 28 days post-inoculation. No vaccinal reaction was seen at the inoculation site with either of the recombinants and the chickens remained healthy through the 28 day observation period.

Groups of ten 28 day old chickens were inoculated with each of the recombinant viruses receiving either 3.0 $\log_{10}$ $TCID_{50}$ by the intra-muscular route or 3.0 $\log_{10}$ $TCID_{50}$ by the cutaneous (wing web) route. Chickens were observed for 28 days and serum samples collected at 14 and 28 days post inoculation. No reaction was seen after intramuscular inoculation with either of the recombinants. Cutaneous inoculation resulted in a very small vaccinal reaction to fowlpox with lesions being heterogenous in size. Canarypox inoculation led to the production of a normal cutaneous lesion at the inoculation site. All lesions had regressed by the end of the experiment.

B. Immune Response

The RFFI test previously described in Example 7 was used to assess the antibody levels to the rabies glycoprotein. For each group, the results were expressed with the geometric mean titer of the individual serum converted to International Units (IU) according to a standard serum which contained 23.4 IU. The minimum positivity level was fixed at one IU and was used to determine the percentage of positive birds. Antibodies against the avipox viruses were tested with an ELISA method using the fowlpox virus strain as an antigen. Each serum sample was diluted at 1/20 and 1/80. A standard curve was constructed using a positive and negative sera. The minimum positivity level was calculated with the mean of the different values of the negative sera added with two standard deviations.

The results of serological surveys are shown in Table XV for vFP-6 and Table XVI for vCP-16.

A limited serological response was observed with embryos inoculated with either vFP-6 or vCP-16 for both rabies and fowlpox antigens. The fowlpox vector induced a serological response to both antigens in a greater number of birds than did canarypox but the response was still heterogenous.

Chickens inoculated at 1-day old with vFP-6 had a good serological response with all birds being seropositive to rabies and fowlpox antigens by 28 days post-inoculation. The response to vCP-16 inoculation was much lower with 40% of birds being seropositive for rabies glycoprotein at 28 days and 10% seropositive for avipox antigens.

Chickens inoculated with vFP-6 by the intramuscular route at 28 days old showed 100% seroconversion to both antigens by 14 days post-inoculation. Although the majority of birds also seroconverted after cutaneous inoculation, titers achieved were lower for both rabies and avipox antigens. As previously, chickens inoculated both by the intramuscular and cutaneous route with vCP-16 showed a variable response with a maximum of 70% seroconversion to rabies by intramuscular inoculation. The low level of seroconversion for avipox antigens after canarypox inoculation may reflect the degree of serological relatedness between the viruses.

The results indicate both vFP-6 and vCP-16 to be safe for inoculation of chickens of a range of ages. The fowlpox vector vFP-6 appears to be more efficient in inducing an immune response in chickens. Significantly, however, both recombinant avipox viruses, fowlpox and canarypox, are shown to be useful for immunization in ovum.

were normal with no difference being apparent between inoculated and uninoculated animals.

Piglets inoculated both by the intramuscular route and oral route developed a serological response to fowlpox antigens as measured by ELISA and serum neutralization. A secondary response was evident after the booster inoculation (results not shown). All piglets also developed an immunological response to rabies glycoprotein as measured in an RFFI test and a booster effect is evident by both routes. These results are shown in Table XVII.

The results indicate that inoculation of a fowlpox/rabies recombinant is innocuous in piglets and that the recombinant is able to produce a significant immune response to the rabies glycoprotein by oral or intramuscular inoculation.

TABLE XV

Immunologic Response Against Fowlpox/Rabies Glycoprotein (vFP-6) in Chickens at Different Ages

| Groups | Dose (TCID50) | Time After Inoculation (Days) | Antibodies | | | |
|---|---|---|---|---|---|---|
| | | | Rabies Glycoprotein | | Fowlpox | |
| | | | Mean IU titer | % birds/1IU | mean Elisa OD | % positive |
| Embryos | $10^3$ | 3 + 14 | 0.28 | 15% | 0.125 | 54% |
| 18 days old | $10^4$ | 3 + 14 | 0.87 | 30% | 0.129 | 46% |
| Chickens 1 day old IM route | $10^3$ | 14 | 1.8 | 90% | 0.109 | 70% |
| | | 28 | 4.2 | 100% | 0.234 | 100% |
| Chickens 28 day old IM route | $10^3$ | 14 | 3.7 | 100% | 0.317 | 100% |
| | | 28 | 2.7 | 100% | 0.378 | 100% |
| Chickens 28 day old transfixion route | $10^3$ | 14 | 1.6 | 100% | 0.191 | 100% |
| | | 28 | 0.54 | 90% | 0.161 | 80% |

TABLE XVI

Immunologic Response Against Canarypox/Rabies Glycoprotein (vCP-16) in Chickens at Different Ages

| Groups | Dose (TCID60) | Time After Inoculation (Days) | Antibodies | | | |
|---|---|---|---|---|---|---|
| | | | Rabies Glycoprotein | | Canarypox | |
| | | | Mean IU titer | % birds/1IU | mean Elisa OD | % positive |
| Embryos | $10^3$ | 3 + 14 | 0.14 | 0% | 0.068 | 25% |
| 18 days old | $10^4$ | 3 + 14 | 0.19 | 8% | 0.059 | 25% |
| Chickens 1 day old IM route | $10^3$ | 14 | 0.18 | 10% | 0.027 | 0% |
| | | 28 | 0.21 | 40% | 0.059 | 10% |
| Chickens 28 day old IM route | $10^3$ | 14 | 0.61 | 70% | 0.093 | 60% |
| | | 28 | 0.24 | 30% | 0.087 | 30% |
| Chickens 28 day old transfixion route | $10^3$ | 14 | 0.34 | 40% | 0.071 | 30% |
| | | 28 | 0.11 | 10% | 0.061 | 10% |

EXAMPLE 25

Safety and Immunogenicity of vFP-6 Inoculation of Piglets

Two groups of three piglets were inoculated with the recombinant vFP-6 by one of two routes:
a) three animals received 8.1 $\log_{10}$ TCID$_{50}$ by intramuscular inoculation; and
b) three animals received the same dose by oral inoculation.

All animals were bled at weekly intervals and received a booster inoculation of the same dose by the same route on day 35. Piglets were observed daily for clinical signs. Sera were tested for antifowlpox antibodies by an ELISA test and a serum neutralization test. Rabies antibodies were assayed in an RFFI test.

All piglets remained in good health and no lesions were observed after inoculation. Temperature curves

TABLE XVII

Antibody to Rabies Glycoprotein Produced in Piglets Inoculated with vFP-6

| Vaccination Route | Animal No. | Rabies Antibody on Days (RFFI Titer) | | | | | |
|---|---|---|---|---|---|---|---|
| | | 14 | 21 | 28 | 35[b] | 42 | 49 |
| I.M. | 984 | 2.4[a] | 2.2 | 2.1 | 2.2 | 3 | 3 |
| | 985 | 2.5 | 2.7 | 2.6 | 2.4 | 3 | 3 |
| | 986 | 2.2 | 2.0 | 2.1 | 2.3 | 3 | 3 |
| Oral | 987 | 3 | 2 | 2.1 | 2 | 3 | 3 |
| | 988 | 2.9 | 2.4 | 2.2 | 2.4 | 2.7 | 2.5 |
| | 989 | 2.8 | 2 | 1.7 | 1.8 | 2.4 | 2.5 |

[a]Titer expressed as $\log_{10}$ of highest serum dilution giving greater than 50% reduction in the number of fluorescing wells in an RFFI test
[b]Animals received second inoculation on day 35

What is claimed is:

1. A method for inducing an immunological response in a mammal to a mammalian pathogen, which method comprises inoculating the mammal with a recombinant avipox virus comprising DNA which codes for and expresses an antigen of the pathogen.

2. A method for inducing an immunological response in a vertebrate to a vertebrate pathogen, which method comprises inoculating the vertebrate with a recombinant avipox virus comprising DNA which codes for and expresses an antigen of the pathogen; wherein the antigen is selected from the group consisting of rabies G antigen, gp51,30 envelope antigen of bovine leukemia virus, FeLV envelope antigen of feline leukemia virus and glycoprotein D antigen of herpes simplex virus.

3. A recombinant avipox virus containing therein DNA from a non-avipox source in a nonessential region of the avipox genome; said DNA coding for an antigen of a mammalian pathogen; and wherein the antigen is selected from the group consisting of rabies antigen, rabies G antigen, gp51,30 envelope antigen of bovine leukemia virus, FeLV envelope antigen of feline leukemia virus and glycoprotein D antigen of herpes simplex virus.

* * * * *